United States Patent [19]
Edwards et al.

[11] Patent Number: 6,071,280
[45] Date of Patent: *Jun. 6, 2000

[54] MULTIPLE ELECTRODE ABLATION APPARATUS

[75] Inventors: Stuart D. Edwards, Portola Valley, Calif.; Ronald G. Lax, Palm City, Fla.; Hugh Sharkey, Redwood Shores, Calif.

[73] Assignee: Rita Medical Systems, Inc., Mountain View, Calif.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/802,195

[22] Filed: Feb. 14, 1997

Related U.S. Application Data

[63] Continuation-in-part of application No. 08/515,379, Aug. 15, 1995, Pat. No. 5,683,384, which is a continuation-in-part of application No. 08/290,031, Aug. 12, 1994, Pat. No. 5,536,267, which is a continuation-in-part of application No. 08/148,439, Nov. 8, 1993, Pat. No. 5,458,597.

[51] Int. Cl.⁷ .................................................. A61B 18/18
[52] U.S. Cl. ............................................. 606/41; 607/101
[58] Field of Search .......................... 606/41, 42, 45–50; 607/100–102, 122, 154, 156; 600/372–374

[56] References Cited

U.S. PATENT DOCUMENTS

| | | |
|---|---|---|
| Re. 32,057 | 12/1985 | Leveen . |
| Re. 32,066 | 1/1986 | Leveen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | Leveen . |
| 4,011,872 | 3/1977 | Komiya . |
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |
| 4,080,959 | 3/1978 | Leveen . |
| 4,085,756 | 4/1978 | Weaver . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 566 450B1 | 10/1993 | European Pat. Off. . |
| 0 608 609 | 8/1994 | European Pat. Off. . |
| 2 283 701 | 4/1976 | France . |
| 2 670 664 | 6/1992 | France . |

(List continued on next page.)

*Primary Examiner*—Michael Peffley
*Attorney, Agent, or Firm*—Wilson, Sonsini, Goodrich & Rosati

[57] ABSTRACT

A tissue ablation apparatus includes a delivery catheter with distal and proximal ends. A handle is attached to the proximal end of the delivery catheter. At least partially positioned in the delivery catheter is an electrode deployment device. The electrode deployment devices includes a plurality of retractable electrodes. Each electrode has a non-deployed state when it is positioned in the delivery catheter. Additionally, each electrode has a distended deployed state when it is advanced out of the delivery catheter distal end. The deployed electrodes define an ablation volume. Each deployed electrode has a first section with a first radius of curvature. The first section is located near the distal end of the delivery catheter. A second section of the deployed electrode extends beyond the first section, ad has a second radius of curvature, or a substantially linear geometry.

46 Claims, 21 Drawing Sheets

U.S. PATENT DOCUMENTS

| | | |
|---|---|---|
| 4,095,602 | 6/1978 | Leveen . |
| 4,119,102 | 10/1978 | Leveen . |
| 4,121,592 | 10/1978 | Whalley . |
| 4,140,130 | 2/1979 | Storm, III . |
| 4,154,246 | 5/1979 | Leveen . |
| 4,230,129 | 10/1980 | Leveen . |
| 4,237,898 | 12/1980 | Whalley . |
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,892 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | Deluca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | Leveen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Vant't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | Leveen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |
| 5,293,869 | 3/1994 | Edwards et al. . |
| 5,295,955 | 3/1994 | Rosen et al. . |

| | | | | | | |
|---|---|---|---|---|---|---|
| 5,300,068 | 4/1994 | Rosar et al. . | | 5,514,130 | 5/1996 | Baker . |
| 5,300,069 | 4/1994 | Hunsberger et al. . | | 5,514,131 | 5/1996 | Edwards . |
| 5,300,099 | 4/1994 | Rudie . | | 5,520,684 | 5/1996 | Imran . |
| 5,304,214 | 4/1994 | Deford et al. . | | 5,531,676 | 7/1996 | Edwards et al. . |
| 5,309,910 | 5/1994 | Edwards et al. . | | 5,531,677 | 7/1996 | Lundquist et al. . |
| 5,313,943 | 5/1994 | Houser et al. . | | 5,536,240 | 7/1996 | Edwards et al. . |
| 5,314,466 | 5/1994 | Stern et al. . | | 5,536,267 | 7/1996 | Edwards et al. . |
| 5,322,503 | 6/1994 | Desai . | | 5,540,655 | 7/1996 | Edwards et al. . |
| 5,328,467 | 7/1994 | Edwards et al. . | | 5,542,915 | 8/1996 | Edwards et al. . |
| 5,334,193 | 8/1994 | Nardella . | | 5,542,916 | 8/1996 | Hirsch et al. . |
| 5,334,206 | 8/1994 | Daikuzono . | | 5,542,928 | 8/1996 | Evans et al. . |
| 5,336,222 | 8/1994 | Durgin, Jr. et al. . | | 5,545,161 | 8/1996 | Imran . |
| 5,342,357 | 8/1994 | Nardella . | | 5,545,171 | 8/1996 | Sharkey et al. . |
| 5,348,554 | 9/1994 | Imran et al. . | | 5,545,193 | 8/1996 | Fleischman et al. . |
| 5,354,296 | 10/1994 | Turkel . | | 5,546,267 | 8/1996 | Frederiksen et al. . |
| 5,363,861 | 11/1994 | Edwards et al. . | | 5,548,597 | 8/1996 | Edwards et al. . |
| 5,365,926 | 11/1994 | Desai . | | 5,549,108 | 8/1996 | Edwards et al. . |
| 5,366,490 | 11/1994 | Edwards et al. . | | 5,549,644 | 8/1996 | Lundquist et al. . |
| 5,368,592 | 11/1994 | Stern et al. . | | 5,551,426 | 9/1996 | Hummel et al. ........................ 600/374 |
| 5,370,675 | 12/1994 | Edwards et al. ......................... 607/101 | | 5,554,110 | 9/1996 | Edwards et al. . |
| 5,370,678 | 12/1994 | Edwards et al. . | | 5,556,377 | 9/1996 | Rosen et al. . |
| 5,383,876 | 1/1995 | Nardella . | | 5,558,672 | 9/1996 | Edwards et al. . |
| 5,383,917 | 1/1995 | Desai et al. ............................ 607/102 | | 5,558,673 | 9/1996 | Edwards et al. . |
| 5,385,544 | 1/1995 | Edwards et al. . | | 5,560,358 | 10/1996 | Arnold et al. . |
| 5,397,339 | 3/1995 | Desai . | | 5,562,703 | 10/1996 | Desai . |
| 5,398,683 | 3/1995 | Edwards et al. . | | 5,599,345 | 2/1997 | Edwards et al. . |
| 5,401,272 | 3/1995 | Perkins . | | 5,599,346 | 2/1997 | Edwards et al. . |
| 5,403,311 | 4/1995 | Abele et al. .............................. 606/49 | | 5,609,151 | 3/1997 | Mulier et al. . |
| 5,405,346 | 4/1995 | Grundy et al. . | | 5,620,481 | 4/1997 | Desai et al. . |
| 5,409,453 | 4/1995 | Lundquist et al. . | | 5,709,224 | 1/1998 | Behl et al. ................................ 606/41 |
| 5,411,025 | 5/1995 | Webster, Jr. . | | | | |
| 5,417,687 | 5/1995 | Nardella . | | | | |
| 5,421,819 | 6/1995 | Edwards et al. . | | | | |
| 5,423,807 | 6/1995 | Milder . | | | | |
| 5,423,808 | 6/1995 | Edwards et al. . | | | | |
| 5,423,811 | 6/1995 | Imran et al. . | | | | |
| 5,433,708 | 7/1995 | Nichols et al. . | | | | |
| 5,435,805 | 7/1995 | Edwards et al. . | | | | |
| 5,437,662 | 8/1995 | Nardella . | | | | |
| 5,437,664 | 8/1995 | Cohen et al. ............................ 606/42 | | | | |

FOREIGN PATENT DOCUMENTS

| | | |
|---|---|---|
| 10 07 960 | 10/1957 | Germany . |
| 2124684 | 11/1972 | Germany . |
| 21 24 684 | 11/1973 | Germany . |
| 89 09 492 U | 3/1990 | Germany . |
| 38 38 840 | 5/1990 | Germany . |
| 39 30 451 | 3/1991 | Germany . |
| 41 00 422 A1 | 7/1992 | Germany . |
| 63-275632 | 10/1988 | Japan . |
| 63-275632 | 11/1988 | Japan . |
| 2-121675 | 5/1990 | Japan . |
| WO 92/10142 | 6/1992 | WIPO . |
| WO 94/04220 | 3/1994 | WIPO . |
| WO 94/10925 | 5/1994 | WIPO . |
| WO 94/11059 | 5/1994 | WIPO . |
| WO 94/17856 | 8/1994 | WIPO . |
| WO 94/25110 | 11/1994 | WIPO . |
| WO 94/26178 | 11/1994 | WIPO . |
| WO 95/19142 | 7/1995 | WIPO . |
| WO 95/25471 | 9/1995 | WIPO . |
| WO 96/04860 | 2/1996 | WIPO . |
| WO 96/29946 | 10/1996 | WIPO . |
| WO 97/06739 | 2/1997 | WIPO . |

Additional U.S. Patents (continued):

| | | |
|---|---|---|
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,462,521 | 10/1995 | Brucker et al. . |
| 5,470,308 | 11/1995 | Edwards et al. . |
| 5,470,309 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,500,012 | 3/1996 | Brucker et al. . |
| 5,505,730 | 4/1996 | Edwards . |
| 5,507,743 | 4/1996 | Edwards et al. . |
| 5,509,419 | 4/1996 | Edwards et al. . |

MULTIPLE ELECTRODE ABLATION APPARATUS

CONTINUING APPLICATION DATA

This application is a continuation-in-part of U.S. Ser. No. 08/515,379, filed Aug. 15, 1995, now U.S. Pat. No. 5,683,384, entitled MULTIPLE ELECTRODE ABLATION APPARATUS, which is a continuation-in-part of U.S. Ser. No. 08/290,031 Aug. 12, 1994 now U.S. Pat. No. 5,536,267, issued Jul. 7, 1996 entitled MULTIPLE ELECTRODE ABLATION APPARATUS, which is a continuation-in-part of U.S. Ser. No. 08/148,439 Nov. 8, 1993 now U.S. Pat. No. 5,458,597, issued Oct. 17, 1995, entitled DEVICE FOR TREATING CANCER AND NON-MALIGNANT TUMORS AND METHODS.

BACKGROUND OF THE INVENTION

1. Field of the Invention

This invention relates generally to an apparatus for the treatment and ablation of body masses, such as tumors, and more particularly, to a retractable multiple needle electrode apparatus that surrounds an exterior of a tumor with a plurality of needle electrodes and defines an ablative volume.

2. Description of Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor, with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna. When it is driven using RF current unwanted surface heating occurs diminishing heating to the underlying tissue.

Thus, non-invasive procedures for providing heat to internal tumors have had difficulties in achieving substantial specific and selective treatment.

Hyperthermia, which can be produced from an RF or microwave source, applies heat to tissue but does not exceed 45 degrees C. so that normal cells survive. In thermotherapy, heat energy of greater than 45 degrees C. is applied, resulting in histological damage, desiccation and the denaturization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related the thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure more effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as disclosed in U.S. Pat. No. 4,920,978. A microwave endoscope device is described in U.S. Pat. No. 4,409,993. In U.S. Pat. No. 4,920,978, an endoscope for RF hyperthermia is disclosed.

In U.S. Pat. No. 4,763,671, a minimally invasive procedure utilizes two catheters that are inserted interstitially into the tumor. The catheters are placed within the tumor volume and each is connect to a high frequency power source.

In U.S. Pat. No. 4,565,200, an electrode system is described in which a single entrance tract cannula is used to introduce an electrode into a selected body site.

However, as an effective treatment device, electrodes must be properly positioned relative to the tumor. After the electrodes are positioned, it is then desirable to have controlled application and deposition of RF energy to ablate the tumor. This reduces destruction of healthy tissue.

There is a need for a RF tumor treatment apparatus that is useful for minimally invasive procedures. It would be desirable for such a device to surround the exterior of the tumor with treatment electrodes, defining a controlled ablation volume, and subsequently the electrodes deliver a controlled amount of RF energy. Additionally, there is a need for a device with infusion capabilities during a pre-ablation step, and after ablation the surrounding tissue can be preconditioned with electromagnetic ("EM") energy at hyperthermia temperatures less than 45 degrees. This would provide for the synergistic affects of chemotherapy and the instillation of a variety of fluids at the tumor site after local ablation and hyperthermia.

SUMMARY OF THE INVENTION

An object of the invention is to provide an RF tissue ablation apparatus which ablates a desired tissue site, such as a tumor, in a minimally invasive manner.

Another object of the invention is to provide an RF tissue ablation apparatus which includes a selectable plurality of retractable electrodes which are advanced from a delivery catheter to define an ablation volume.

A further object of the invention is to provide an RF tissue ablation apparatus which includes a plurality of electrodes that are retractable to and from a delivery catheter. The electrodes are at least partially positioned in the delivery catheter in a non-deployed state, and become distended in a deployed state when advanced out a distal end of the delivery catheter, defining the ablation volume.

Another object of the invention is to provide an RF tissue ablation apparatus with deployed electrodes having a first section with a first radius of curvature, and a second section, that extends beyond the first section, having a second radius of curvature or a substantially linear geometry.

Yet another object of the invention is to provide an RF tissue ablation apparatus with deployed electrodes with two or more radii of curvature.

Still another object of the invention is to provide an RF tissue ablation apparatus with deployed electrodes having at least one radii of curvature in two or more planes.

A further object of the invention is to provide an RF tissue ablation apparatus with at least one deployed electrode that has one curved section located near a distal end of the delivery catheter, and a non-curved section extending beyond the curved section of the deployed electrode. The ablation apparatus also includes at least one deployed electrode with at least two radii of curvature.

Yet another object of the invention is to provide a tissue ablation apparatus with a plurality of retractable electrodes, each deployed electrode has at least one curved section located near a distal end of a delivery catheter, and a non-curved section which extends beyond the curved section of the deployed electrode.

These and other objects are attained with a tissue ablation apparatus that includes a delivery catheter, with distal and proximal ends. A handle is attached to the proximal end of the delivery catheter. An electrode deployment apparatus is positioned at least partially in the delivery catheter. It includes a plurality of electrodes that are retractable in and out of the catheter's distal end. The electrodes are in a non-deployed state when they are positioned within the delivery catheter. As they are advanced out the distal end of the catheter they become deployed, and define an ablation volume. Each electrode has a first section with a first radius of curvature, and a second section, extending beyond the first section, having a second radius of curvature or a substantially linear geometry.

Alternatively, each deployed electrode has at least two radii of curvature that are formed when the needle is advanced through the delivery catheter's distal end and becomes positioned at a selected tissue site.

In another embodiment, each deployed electrode has at least one radius of curvature in two or more planes. Further, the electrode deployment apparatus can include at least one deployed electrode having at least radii of curvature, and at least one deployed electrode with at least one radius of curvature in two or more planes.

In a further embodiment, the electrode deployment apparatus has at least one deployed electrode with at least one curved section that is located near the distal end of the delivery catheter, and a non-curved section which extends beyond the curved section of the deployed electrode. The electrode deployment apparatus also has at least one deployed electrode with at least two radii of curvature.

In another embodiment of the invention, each deployed electrode has at least one curved section located near the distal end of the delivery catheter, and a non-curved section that extends beyond the curved section of the deployed electrode.

An electrode template can be positioned at the distal end of the delivery catheter. It assists in guiding the deployment of the electrodes to a surrounding relationship at an exterior of a selected mass in a tissue. The electrodes can be hollow. An adjustable electrode insulator can be positioned in an adjacent, surrounding relationship to all or some of the electrodes. The electrode insulator is adjustable, and capable of being advanced and retracted along the electrodes in order to define an electrode conductive surface.

The electrode deployment apparatus can include a cam which advances and retracts the electrodes in and out of the delivery catheter's distal end. Optionally included in the delivery catheter are one or more guide tubes associated with one or more electrodes. The guide tubes are positioned at the delivery catheter's distal end.

Sources of infusing mediums, including but not limited to electrolytic and chemotherapeutic solutions, can be associated with the hollow electrodes. Electrodes can have sharpened, tapered ends in order to assist their introduction through tissue, and advancement to the selected tissue site.

The electrode deployment apparatus is removable from the delivery catheter. An obturator is initially positioned within the delivery catheter. It can have a sharpened distal end. The delivery catheter can be advanced percutaneously to an internal body organ, or site, with the obturator positioned in the delivery catheter. Once positioned, the obturator is removed, and the electrode deployment apparatus is inserted into the delivery catheter. The electrodes are in non-deployed states, and preferably compacted or spring-loaded, while positioned within the delivery catheter. They are made of a material with sufficient strength so that as the electrodes emerge from the delivery catheter's distal end they are deployed three dimensionally, in a lateral direction away from the periphery of the delivery catheter's distal end. The electrodes continue their lateral movement until the force applied by the tissue causes the needles to change their direction of travel.

Each electrode now has either, (i) a first section with a first radius of curvature, and a second section, extending beyond the first section, having a second radius of curvature or a substantially linear section, (ii) two radii of curvature, (iii) one radius of curvature in two or more planes, or (iv) a combination of two radii of curvature with one of them in two or more planes. Additionally, the electrode deployment apparatus can include one or more of these deployed geometries for the different electrodes in the plurality. It is not necessary that every electrode have the same deployed geometry.

After the electrodes are positioned around a mass, such as a tumor, a variety of solutions, including but not limited to electrolytic fluids, can be introduced through the electrodes to the mass in a pre-ablation step. RF energy is applied, and the mass is desiccated. In a post-ablation procedure, a chemotherapeutic agent can then be introduced to the site, and the electrodes are then retracted back into the introducing catheter. The entire ablative apparatus can be removed, or additional ablative treatments be conducted.

DETAILED DESCRIPTION

Figure 1:
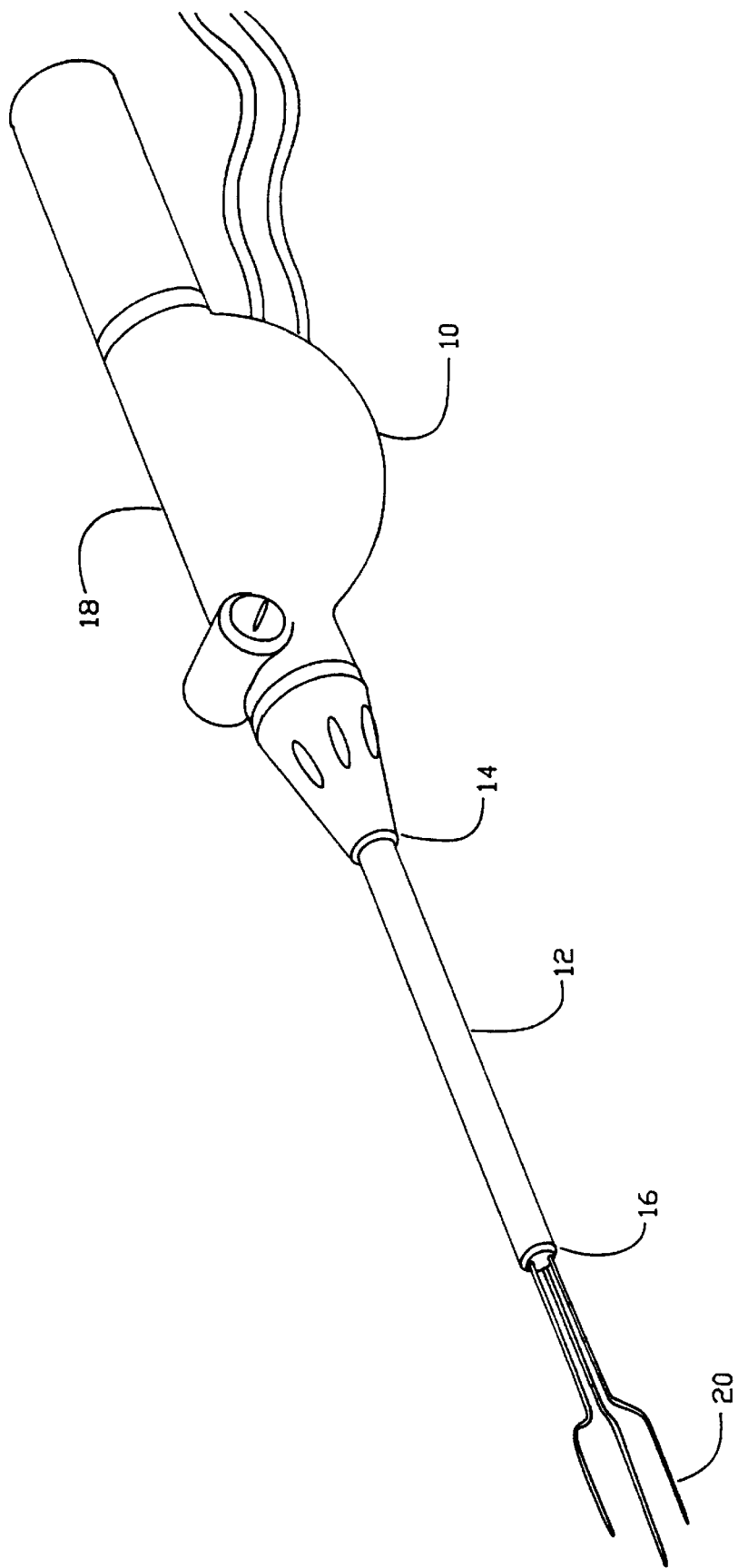
FIG. 1 is a perspective view of the tissue ablation apparatus of the invention, including a delivery catheter, handle, and deployed electrodes.

A tissue ablation apparatus 10 of the invention is illustrated in FIG. 1. Ablation apparatus 10 includes a delivery catheter 12, well known to those skilled in the art, with a proximal end 14 and a distal end 16. Delivery catheter 12 can be of the size of about 5 to 16 F. A handle 18 is removably attached to proximal end 14. An electrode deployment device is at least partially positioned within delivery catheter 12, and includes a plurality of electrodes 20 that are retractable in and out of distal end 16. Electrodes 20 can be of different sizes, shapes and configurations. In one embodiment, they are needle electrodes, with sizes in the range of 27 to 14 gauge. Electrodes 20 are in non-deployed positions while retained in delivery catheter. In the non-deployed positions, electrodes 20 may be in a compacted state, spring loaded, generally confined or substantially straight if made of a suitable memory metal such as nitinol. As electrodes 20 are advanced out of distal end 16 they become distended in a deployed state, which defines an ablative volume, from which tissue is ablated as illustrated more fully in FIG. 2. Electrodes 20 operate either in the bipolar or monopolar modes. When the electrodes are used in the bipolar mode, the ablative volume is substantially defined by the peripheries of the plurality of electrodes 20. In one embodiment, the cross-sectional width of the ablative volume is about 4 cm. However, it will be appreciated that different ablative volumes can be achieved with tissue ablation apparatus 10.

The ablative volume is first determined to define a mass, such as a tumor, to be ablated.

Electrodes 20 are placed in a surrounding relationship to a mass or tumor in a predetermined pattern for volumetric ablation. An imaging system is used to first define the volume of the tumor or selected mass. Suitable imaging systems include but are not limited to, ultrasound, computerized tomography (CT) scanning, X-ray film, X-ray fluoroscopy, magnetic resonance imaging, electromagnetic imaging, and the like. The use of such devices to define a volume of a tissue mass or a tumor is well known to those skilled in the art.

With regard to the use of ultrasound, an ultrasound transducer transmits ultrasound energy into a region of interest in a patient's body. The ultrasound energy is reflected by different organs and different tissue types. Reflected energy is sensed by the transducer, and the resulting electrical signal is processed to provide an image of the region of interest. In this way, the ablation volume is then ascertained, and the appropriate electrode deployment device is inserted into delivery catheter 12.

The ablative volume is substantially defined before ablation apparatus 10 is introduced to an ablative treatment position. This assists in the appropriate positioning of ablation apparatus 10. In this manner, the volume of ablated tissue is reduced and substantially limited to a defined mass or tumor, including a certain area surrounding such a tumor, that is well controlled and defined. A small area around the tumor is ablated in order to ensure that all of the tumor is ablated.

Figure 2:
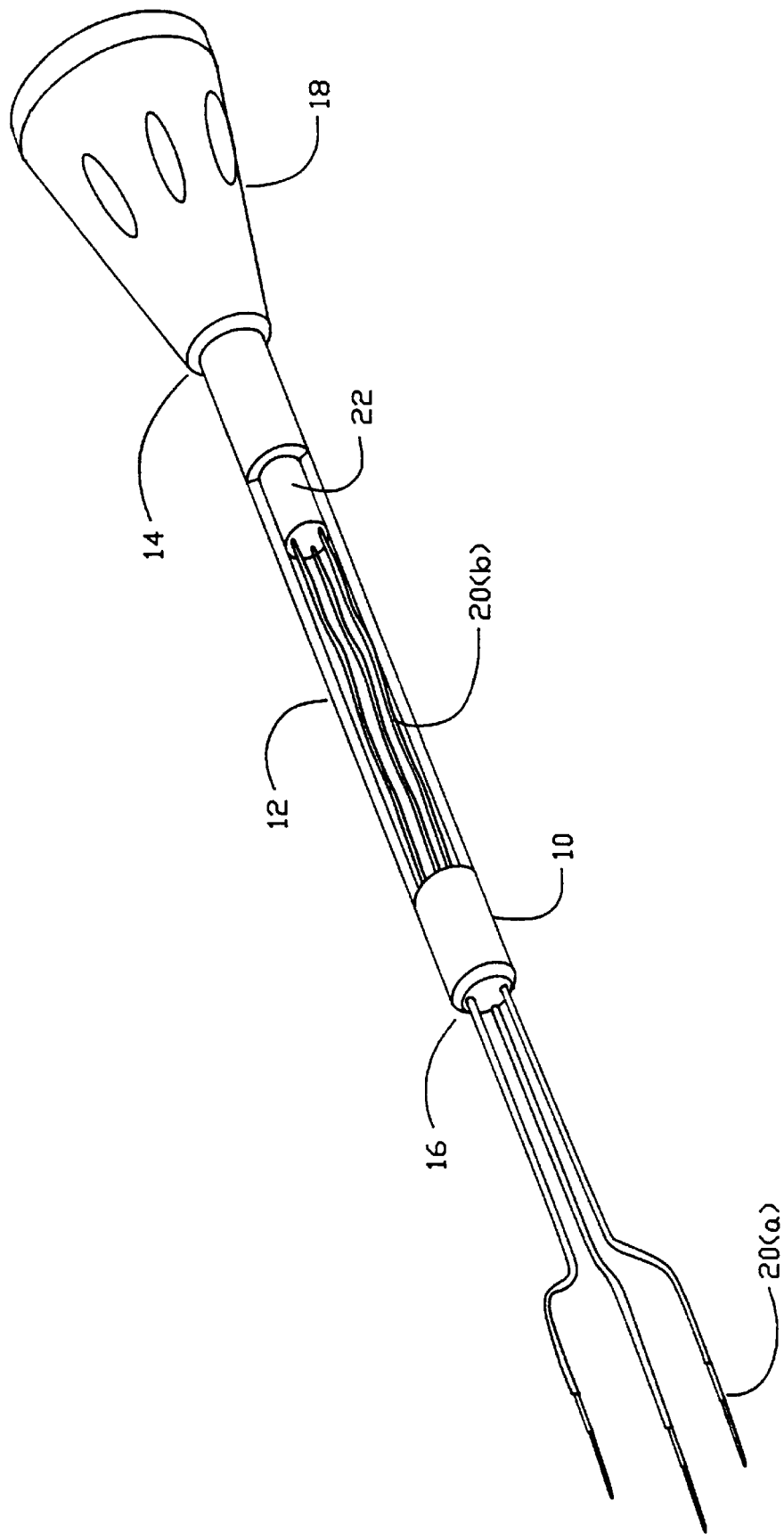
FIG. 2 is a cross-sectional view of the tissue ablation apparatus of the invention illustrated in FIG. 1.

With reference again to FIG. 2, electrode sections 20(a) are in deployed states when they are introduced out of distal end 16. Although electrodes 20 are generally in a non-distended configuration in the non-deployed state while positioned in delivery catheter 12, they can also be distended. Generally, electrode sections 20(b) are in retained positions while they are non-deployed. This is achieved by a variety of methods including but not limited to, (i) the electrodes are pre-sprung, confined in delivery catheter 12, and only become sprung (expanded) as they are released from delivery catheter 12, (ii) the electrodes are made of a memory metal, as explained in further detail below, (iii) the electrodes are made of a selectable electrode material which gives them an expanded shape outside of delivery catheter 12, or (iv) delivery catheter 12 includes guide tubes which serve to confine electrodes 12 within delivery catheter 12 and guide their direction of travel outside of the catheter to form the desired, expanded ablation volume. As shown in FIG. 2, electrodes 20 are pre-sprung while retained in delivery catheter 12. This is the non-deployed position. As they are advanced out of delivery catheter 12 and into tissue, electrodes 20 become deployed and begin to "fan" out from distal end 16, moving in a lateral direction relative to a longitudinal axis of delivery catheter 12. As deployed electrodes 20 continue their advancement, the area of the fan increases and extends beyond the diameter of distal end 16.

Significantly, each electrode 20 is distended in a deployed position, and collectively, the deployed electrodes 20 define a volume of tissue that will be ablated. As previously mentioned, when it is desired to ablate a tumor, either benign or malignant, it is preferable to ablate an area that is slightly in excess to that defined by the exterior surface of the tumor. This improves the chances that all of the tumor is eradicated.

Deployed electrodes 20 can have a variety of different deployed geometries including but not limited to, (i) a first section with a first radius of curvature, and a second section, extending beyond the first section, having a second radius of curvature or a substantially linear geometry, (ii) at least two radii of curvature, (iii) at least one radius of curvature in two or more planes, (iv) a curved section, with an elbow, that is located near distal end 16 of delivery catheter, and a non-curved section that extends beyond the curved section, or (v) a curved section near distal end 16, a first linear section, and then another curved section or a second linear section that is angled with regard to the first linear section. Deployed electrodes 20 need not be parallel with respect to each other. The plurality of deployed electrodes 20, which define a portion of the needle electrode deployment device, can all have the same deployed geometries, i.e., all with at least two radii of curvature, or a variety of geometries, i.e., one with two radii of curvature, a second one with one radius of curvature in two planes, and the rest a curved section near distal end 16 of delivery catheter 12 and a non-curved section beyond the curved section.

A cam 22, or other actuating device, can be positioned within delivery catheter and used to advance and retract electrodes 20 in and out of delivery catheter 12. The actual movement of cam can be controlled at handle 18. Suitable cams are of conventional design, well known to those skilled in the art.

Figure 3:
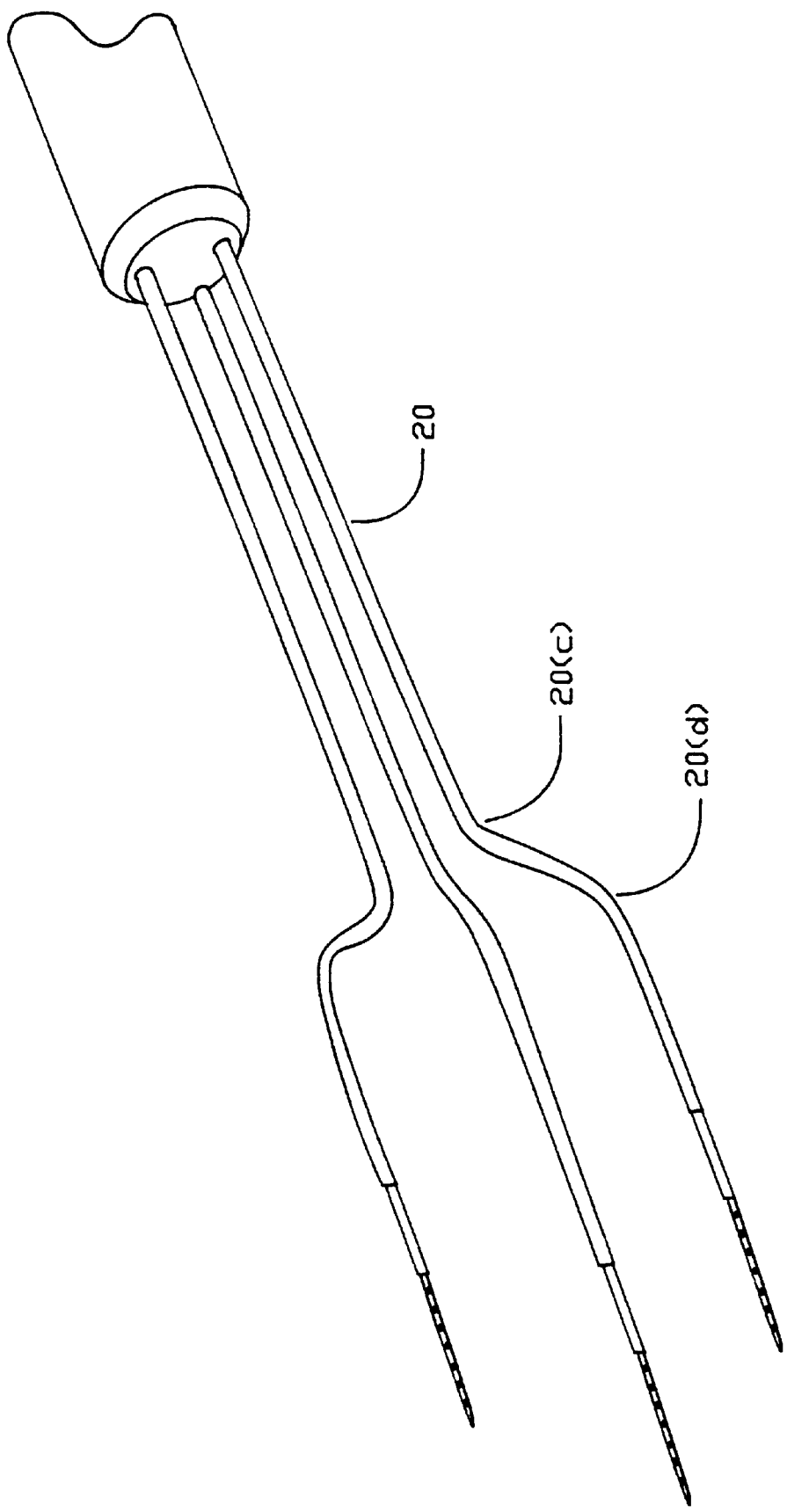
FIG. 3 is a perspective view of an electrode of the invention with two radii of curvature.
Figure 4:
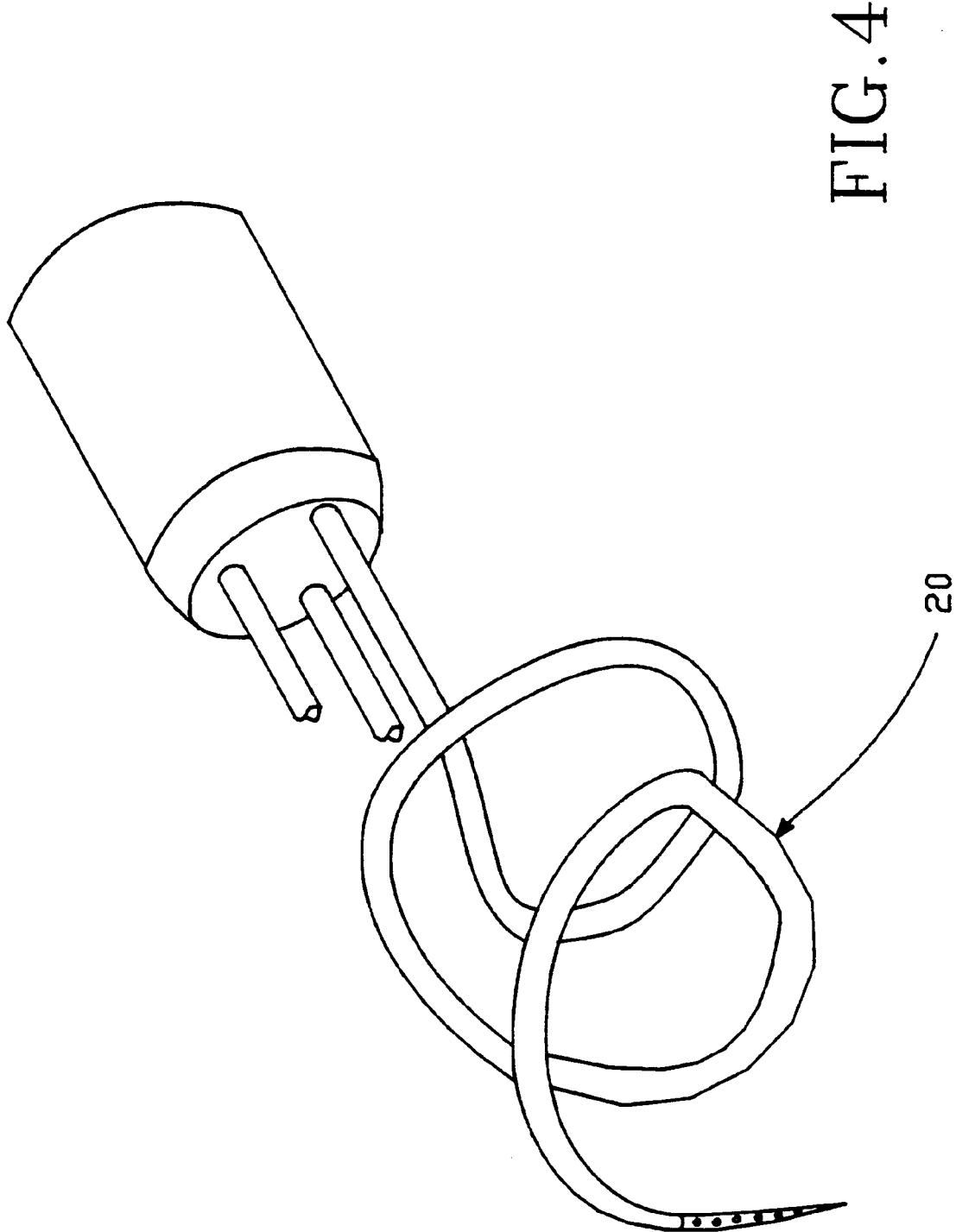
FIG. 4 is a perspective view of an electrode of the invention with one radius of curvature in three planes.
Figure 5:
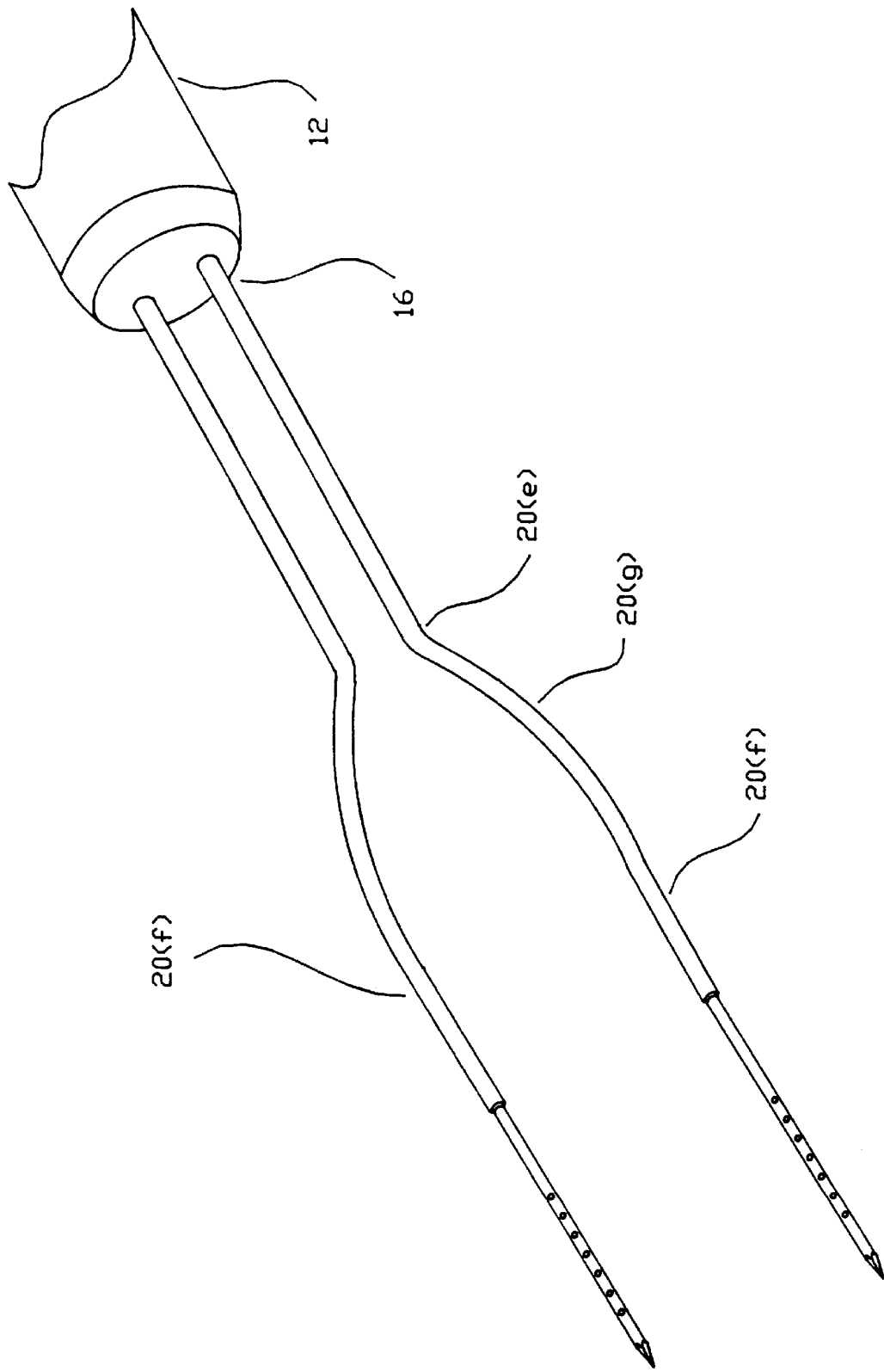
FIG. 5 is a perspective view of an electrode of the invention with one curved section, positioned close to the distal end of the delivery catheter, and a linear section.
Figure 6:
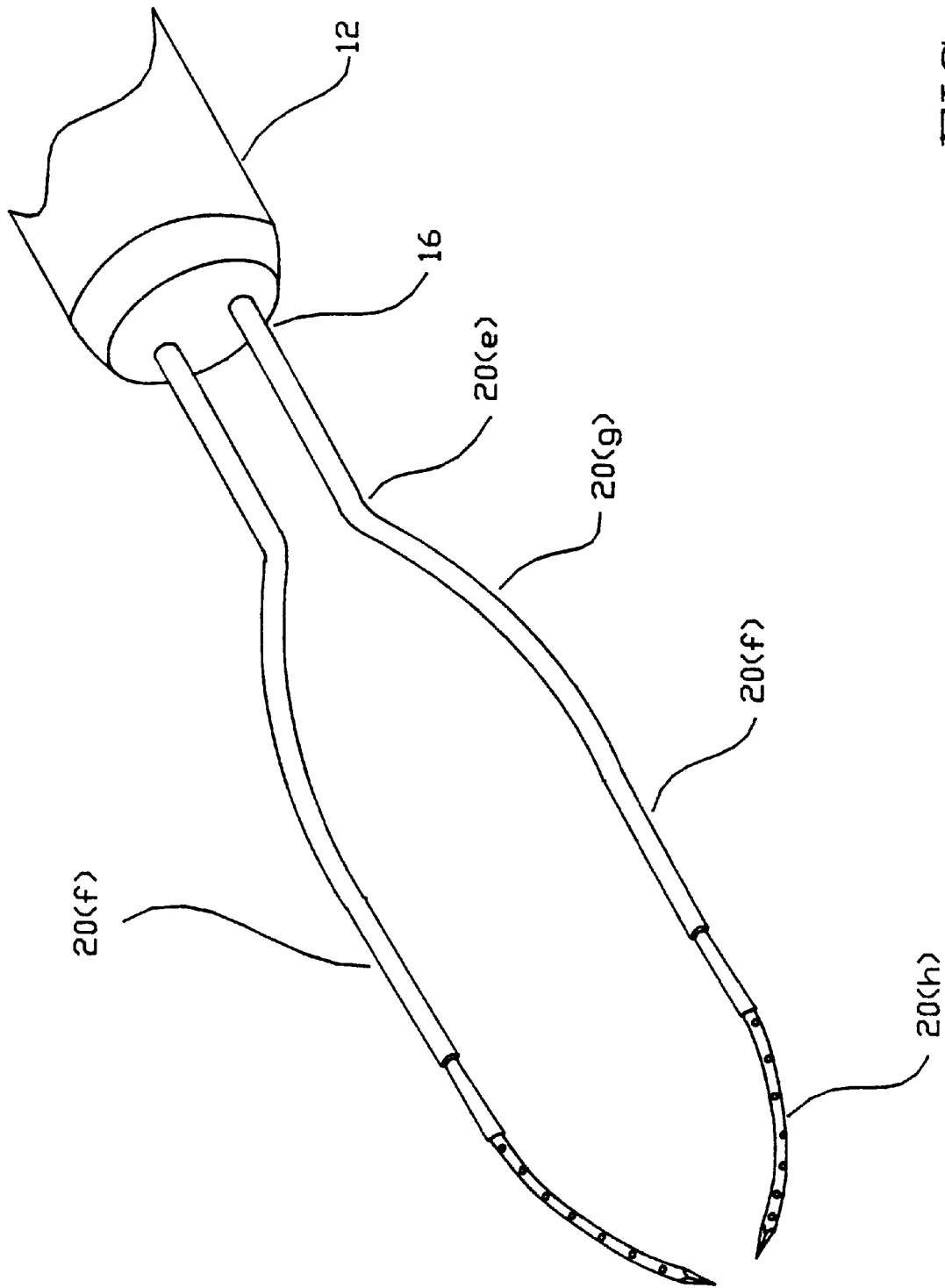
FIG. 6 is a perspective view of an electrode of the invention with one curved section, positioned close to the distal end of the delivery catheter, a generally first linear section, and then a second linear section that continues laterally with regard to the first linear section.

The different geometric configurations of electrodes 20 are illustrated in FIGS. 3 through 6. In FIG. 3, electrode 20 has a first radius of curvature 20(c) and a second radius of curvature 20(d). It can include more than two radii of curvature. As shown in FIG. 4, electrode 20 has at least one radius of curvature which extends to three planes. In FIG. 5, each electrode has a first curved section 20(e) which is near distal end 16 of delivery catheter 12. A first generally linear section 20(f) extends beyond curved section 20(e), and the two meet at an elbow 20(g). The electrodes 20 can serve as anodes and cathodes. The plurality of electrodes 20 can have linear sections 20(f) that are generally parallel to each other, or they can be non-parallel. FIG. 6 illustrates an electrode 20 that includes a first curved section 20(e) positioned near distal end 16 of delivery catheter 12, a first linear section 20(f), and a second linear section 20(h) which extends beyond first linear section 20(f). Section 20(h) can be linear, curved, or a combination of the two. The plurality of electrodes 20 illustrated in FIG. 6 can have parallel or non-parallel first linear sections 20(f).

In one embodiment of the invention, electrodes 20 are spring-loaded, and compacted in their non-deployed positions. As electrodes 20 are advanced out of distal end 16 of delivery catheter 12, they become deployed and fan out. Electrodes 20 continue this fanning out direction until the resistance of the tissue overcomes the strength of the material forming electrode 20. This causes electrode 20 to bend and move in a direction inward relative to its initial outward fanning direction. The bending creates curved sections 20(c) and 20(d) of FIG. 3, and can also result in the formation of the other electrode 20 geometries of FIGS. 4, 5 and 6. The extent of electrode 20 fan like travel is dependent on the strength of the material from which it is made. Suitable electrode materials include stainless steel, platinum, gold, silver, copper and other electromagnetic conducting materials including conductive polymers. Preferably, electrode 20 is made of stainless steel or nickel titanium and has dimensions of about 27 to 14 gauge.

In one embodiment, electrode 20 is made of a memory metal, such as nickel titanium, commercially available from Raychem Corporation, Menlo Park, Calif. Additionally, a resistive heating element can be positioned in an interior lumen of electrode 20. Resistive heating element can be made of a suitable metal that transfers heat to electrode 20, causing deployed electrode 20 to become deflected when the temperature of electrode 20 reaches a level that causes the electrode material, such as a memory metal, to deflect, as is well known in the art. Not all of electrode 20 need be made of a memory metal. It is possible that only that distal end portion of electrode 20, which is introduced into tissue, be made of the memory metal in order to effect the desired deployed geometrical configuration. Additionally, mechanical devices, including but not limited to steering wires, can be attached to the distal end of electrode 20 to cause it to become directed, deflected and move about in a desired direction about the tissue, until it reaches its final resting position to ablate a tissue mass.

Figure 7:
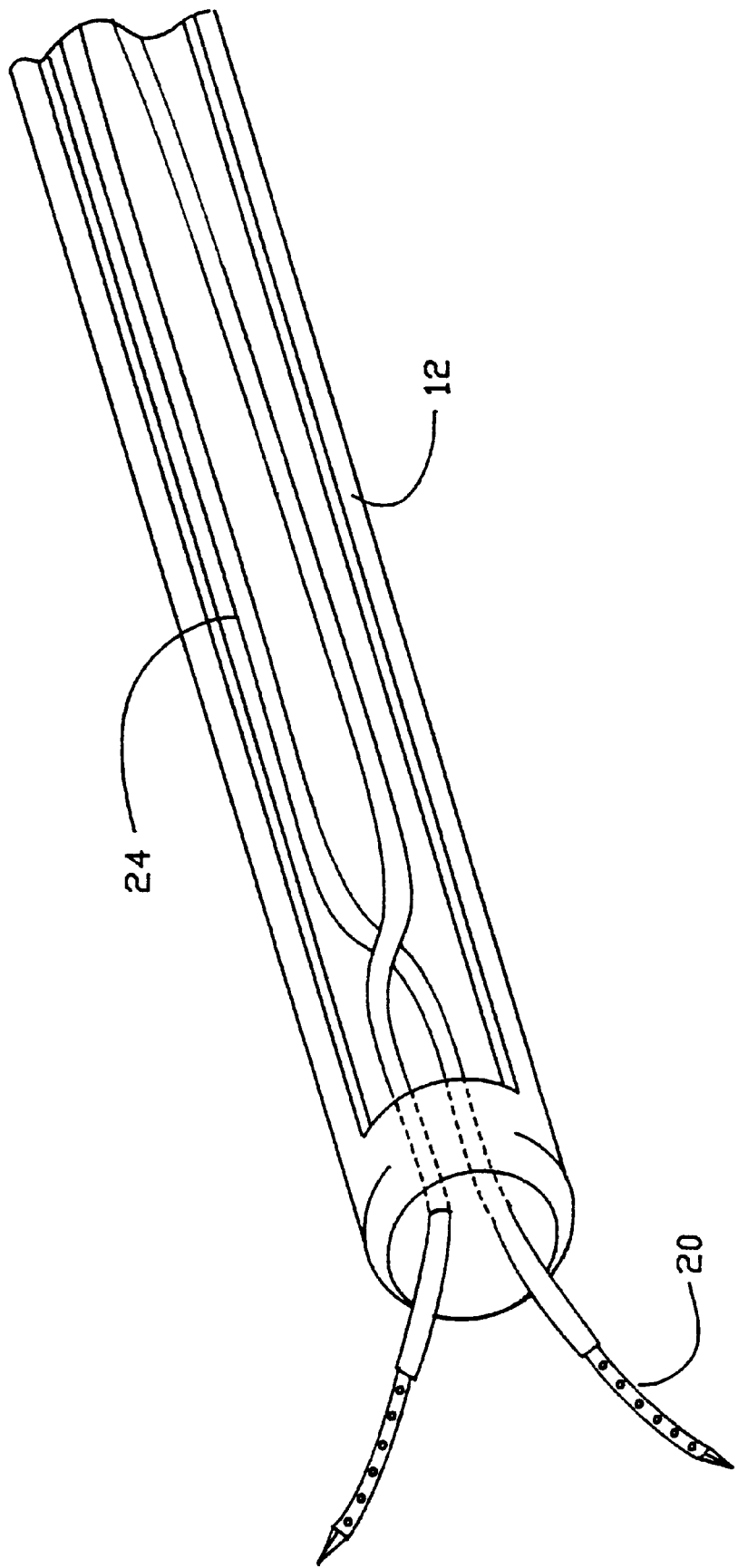
FIG. 7 is a cross-section view of a delivery catheter associated with the invention, with guide tubes positioned at the distal end of the delivery catheter.

Optionally included in the delivery catheter are one or more guide tubes 24, FIG. 7, which serve to direct the expansion of electrodes 20 in the fan pattern as they are advanced out of distal end 16 of the delivery catheter 12. Guide tubes 24 can be made of stainless steel, spring steel and thermal plastics including but not limited to nylon and polyesters, and are of sufficient size and length to accommodate the electrodes to a specific site in the body.

Figure 8:
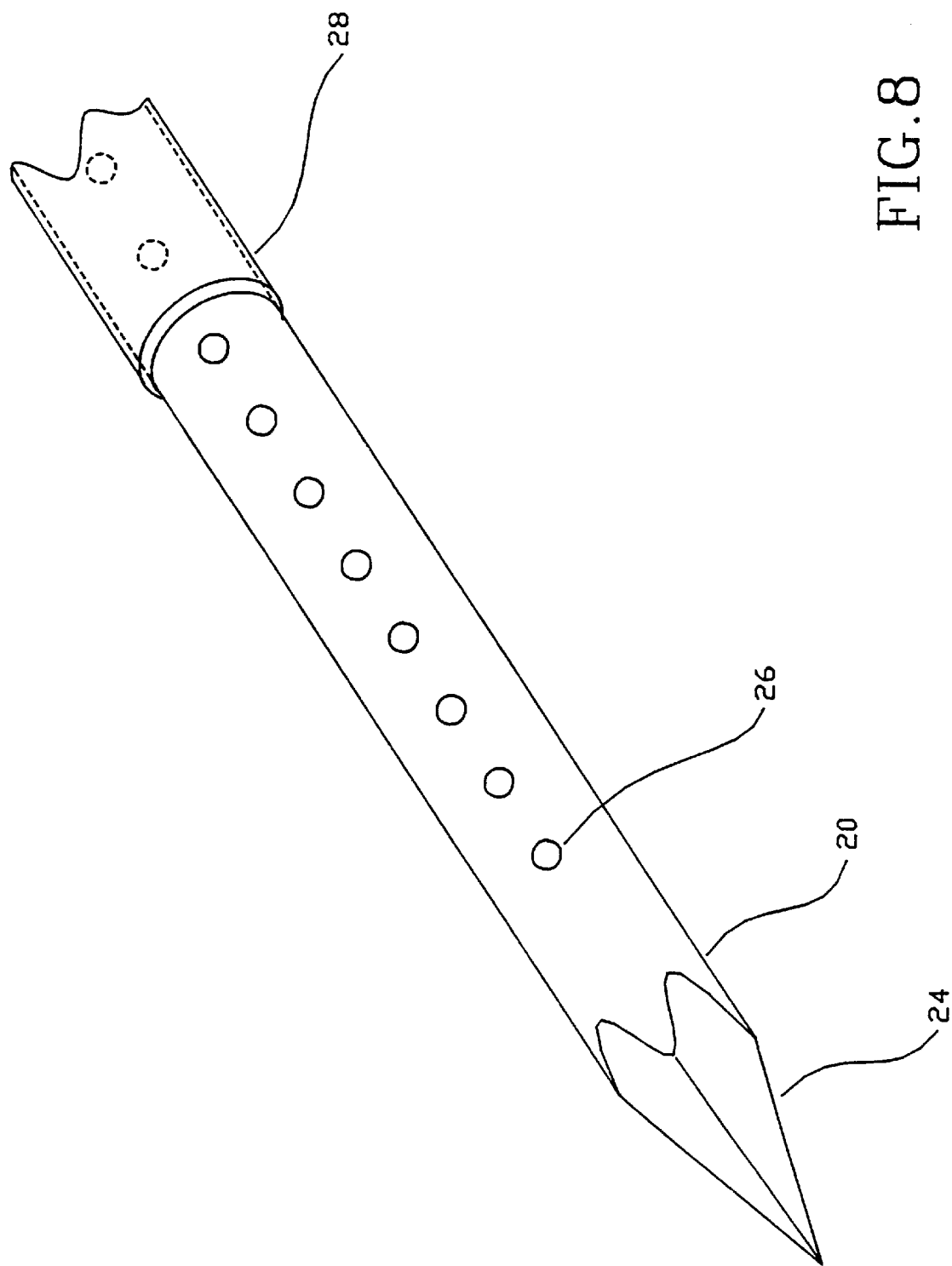
FIG. 8 is a cross-sectional view of an electrode of the invention.

FIG. 8 illustrates one embodiment of electrode 20 with a sharpened distal end 24. By including a tapered, or piercing end 24, the advancement of electrode 20 through tissue is easier. Electrode 20 can be segmented, and include a plurality of fluid distribution ports 26, which can be evenly formed around all or only a portion of electrode 20. Fluid distribution ports 26 are formed in electrode 20 when it is hollow and permit the introduction and flow of a variety of fluidic mediums through electrode 20 to a desired tissue site.

Such fluidic mediums include, but are not limited to, electrolytic solutions, pastes or gels, as well as chemotherapeutic agents. Examples of suitable conductive gels are carboxymethyl cellulose gels made from aqueous electrolyte solutions such as physiological saline solutions, and the like.

The size of fluid distribution ports 26 can vary, depending on the size and shape of electrode 20. Also associated with electrode 20 is an adjustable insulator sleeve 28 that is sidable along an exterior surface of electrode 20. Insulator sleeve 28 is advanced and retracted along electrode 20 in order to define the size of a conductive surface of electrode 20. Insulator sleeve 28 is actuated at handle 18 by the physician, and its position along electrode 20 is controlled. When electrode 20 moves out of delivery catheter 12 and into tissue, insulator sleeve 28 can be positioned around electrode 20 as it moves its way through the tissue.

Alternatively, insulator sleeve 28 can be advanced along a desired length of electrode 20 after electrode 20 has been positioned around a targeted mass to be ablated. Insulator sleeve is thus capable of advancing through tissue along with electrode 20, or it can move through tissue without electrode 20 providing the source of movement. Thus, the desired ablation volume is defined by deployed electrodes 20, as well as the positioning of insulator sleeve 28 on each electrode. In this manner, a very precise ablation volume is created. Suitable materials that form insulator sleeve include but are not limited to nylon, polyimides, other thermoplastics, and the like.

Figure 9:
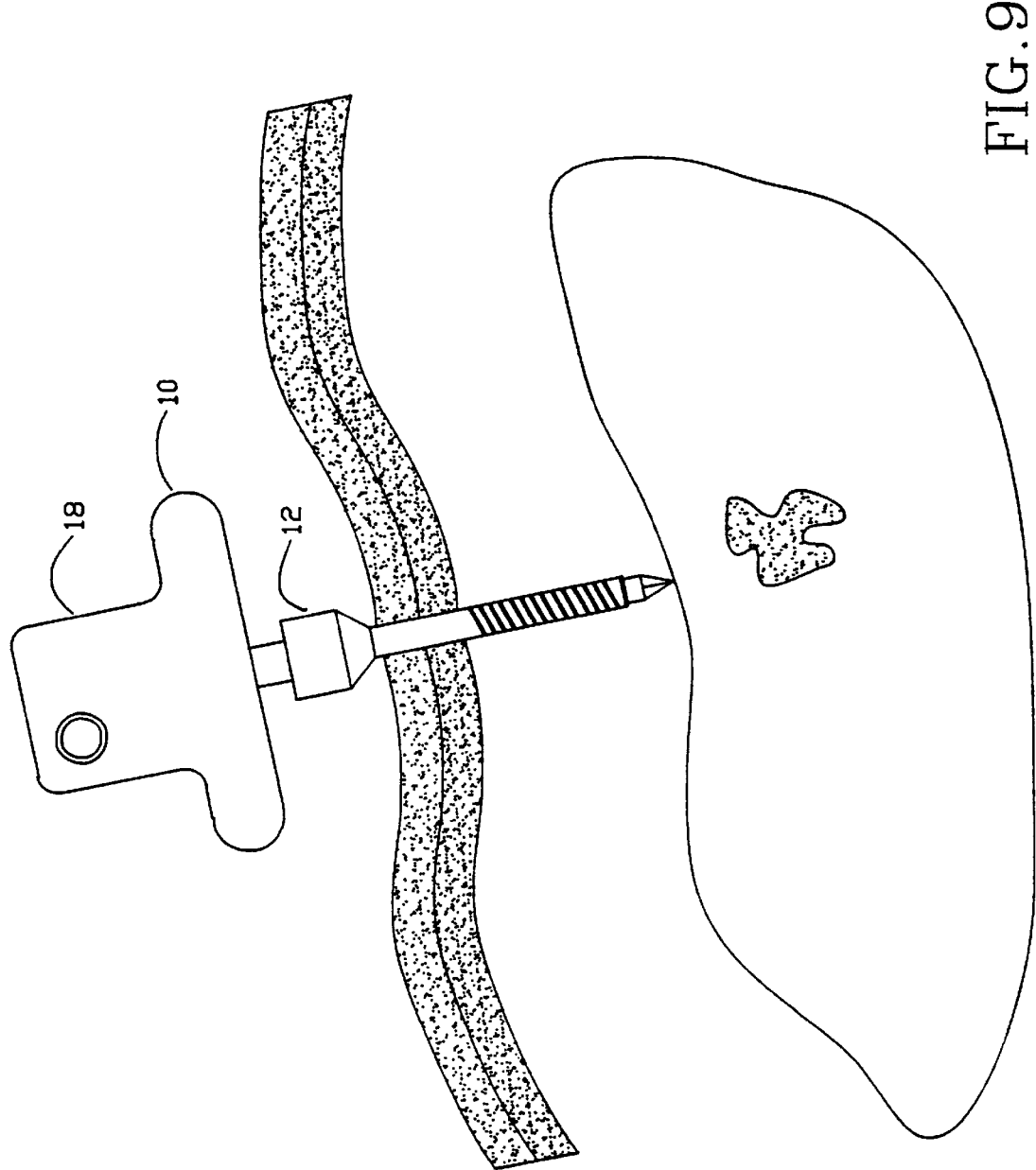
FIG. 9 is a perspective view of the tissue ablation apparatus of the invention shown in FIG. 1, with the delivery catheter being introduced percutaneously through the body and positioned at the exterior, or slightly piercing, a liver with a tumor to be ablated.
Figure 10:
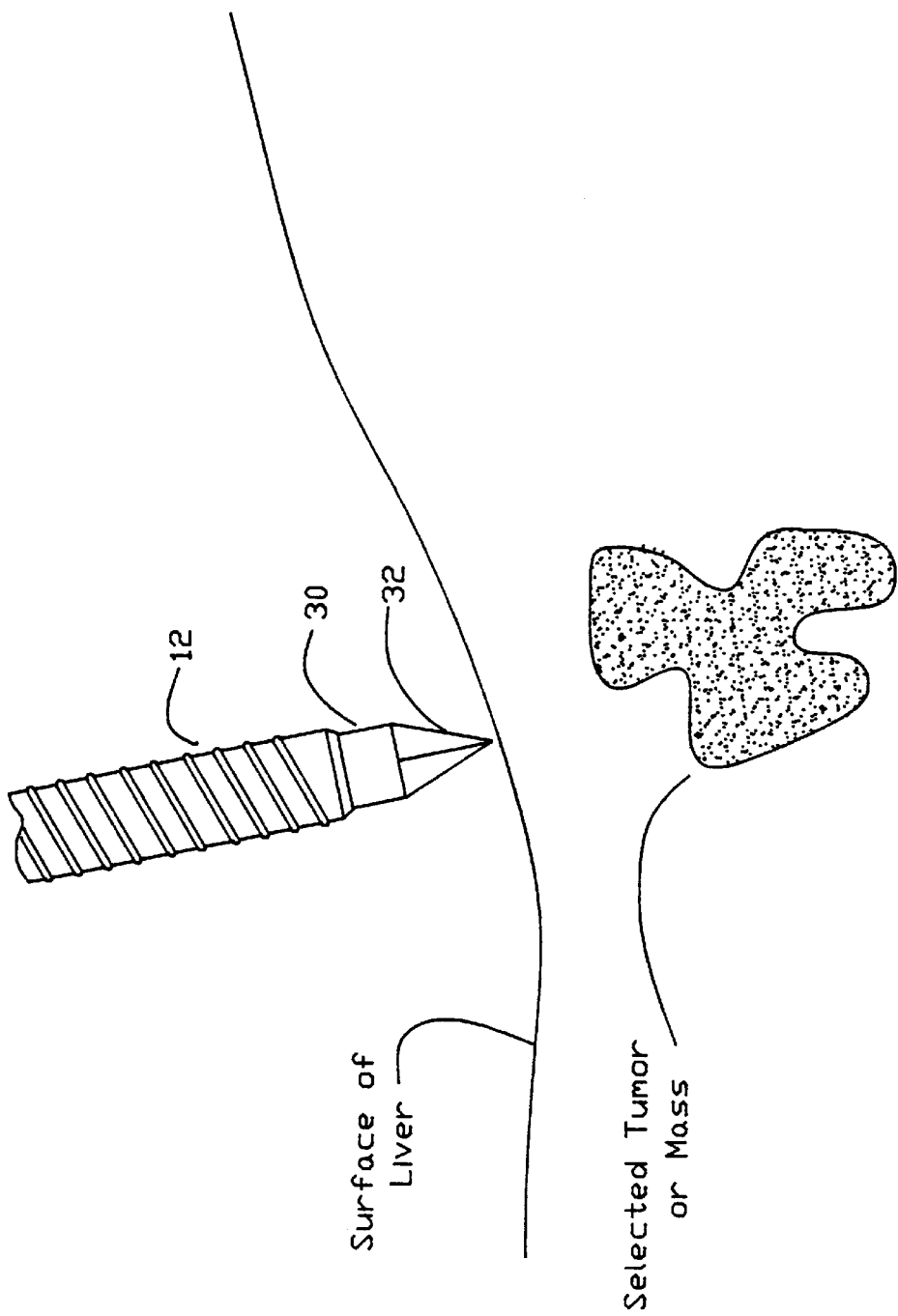
FIG. 10 is a perspective view of the tissue ablation apparatus of the invention with an obturator positioned in the delivery catheter.

FIG. 9 illustrates a percutaneous application of tissue ablation apparatus 10. Tissue ablation apparatus 10 can be used percutaneously to introduce electrodes 20 to the selected tissue mass or tumor. Electrodes 20 can remain in their non-deployed positions while being introduced percutaneously into the body, and delivered to a selected organ which contains the selected mass to be ablated. Delivery catheter 12 is removable from handle 18. When it is removed, electrode deployment device (the plurality of electrodes 20) can be inserted and removed from delivery catheter 12. An obturator 30 is inserted into delivery catheter 12 initially if a percutaneous procedure is to be performed. As shown in FIG. 10, obturator 30 can have a sharpened distal end 32 that pierces tissue and assists the introduction of delivery catheter 12 to a selected tissue site. The selected tissue site can be a body organ with a tumor or other mass, or the actual tumor itself.

Figure 11:
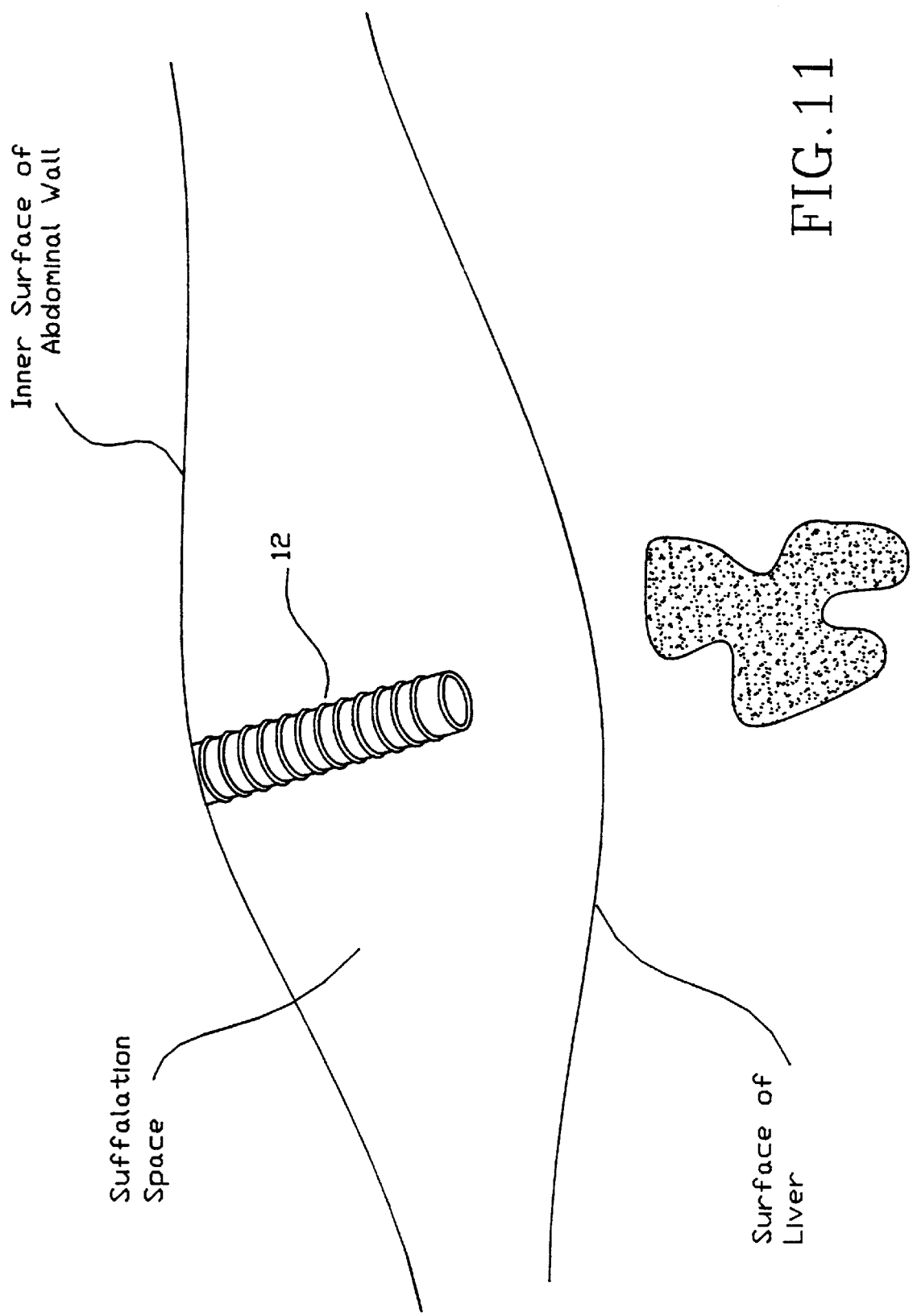
FIG. 11 is a perspective view of the tissue ablation apparatus of the invention shown in FIG. 10, positioned in the body adjacent to the liver, with the obturator removed.
Figure 12:
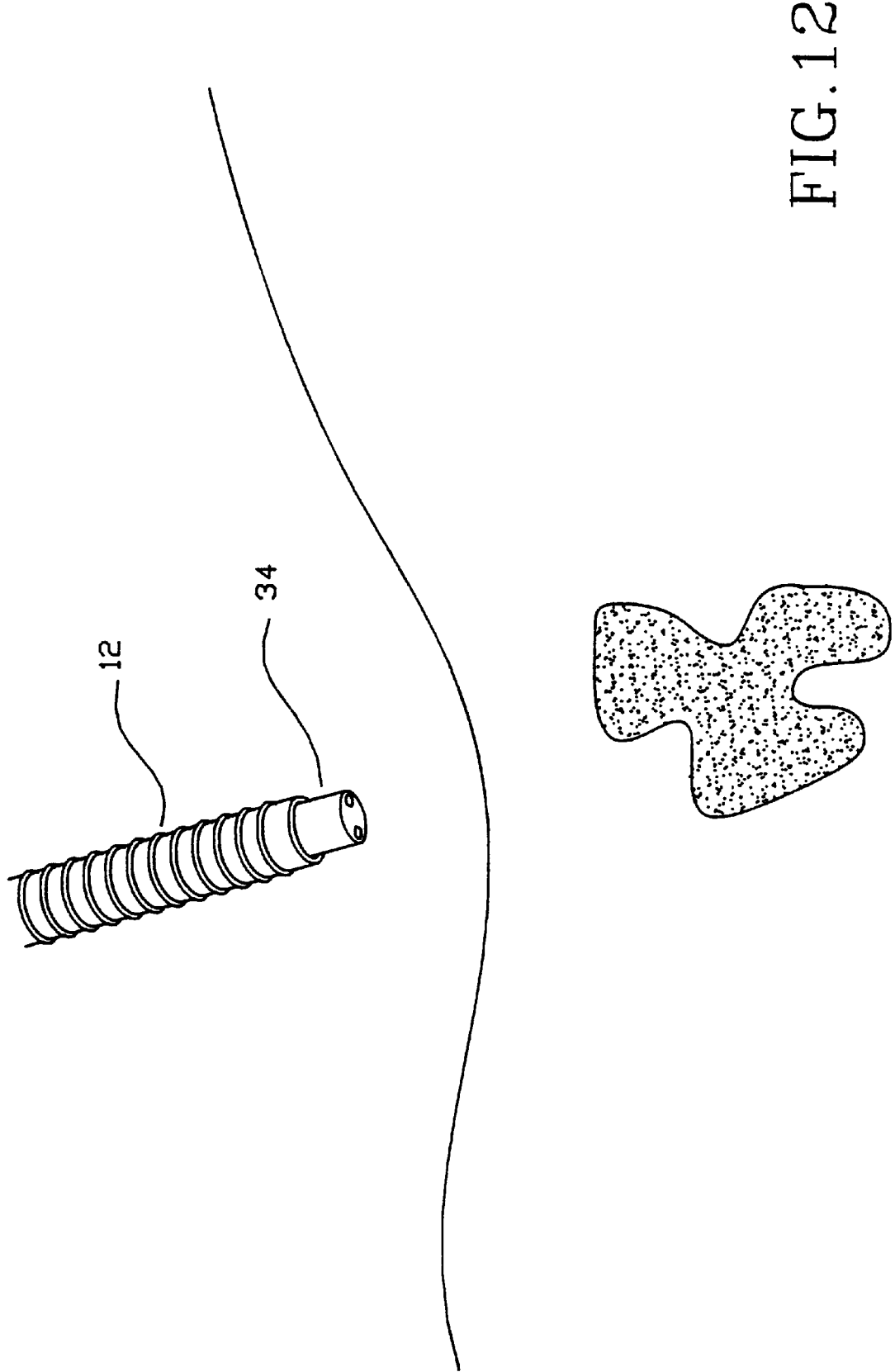
FIG. 12 is a perspective view of the tissue ablation apparatus of the invention shown in FIG. 10, positioned in the body adjacent to the liver, and the electrode deployment apparatus, with an electrode template, is positioned in the delivery catheter in place of the obturator.

Obturator 30 is then removed from delivery catheter 12 (FIG. 11). Electrode deployment device is then inserted into delivery catheter 12, and the catheter is then reattached to handle 18 (FIG. 12). As illustrated in FIG. 12, electrode deployment device can optionally include an electrode template 34 to guide the deployment of electrodes 20 to a surrounding relationship at an exterior of a selected mass in the tissue.

Figure 13:
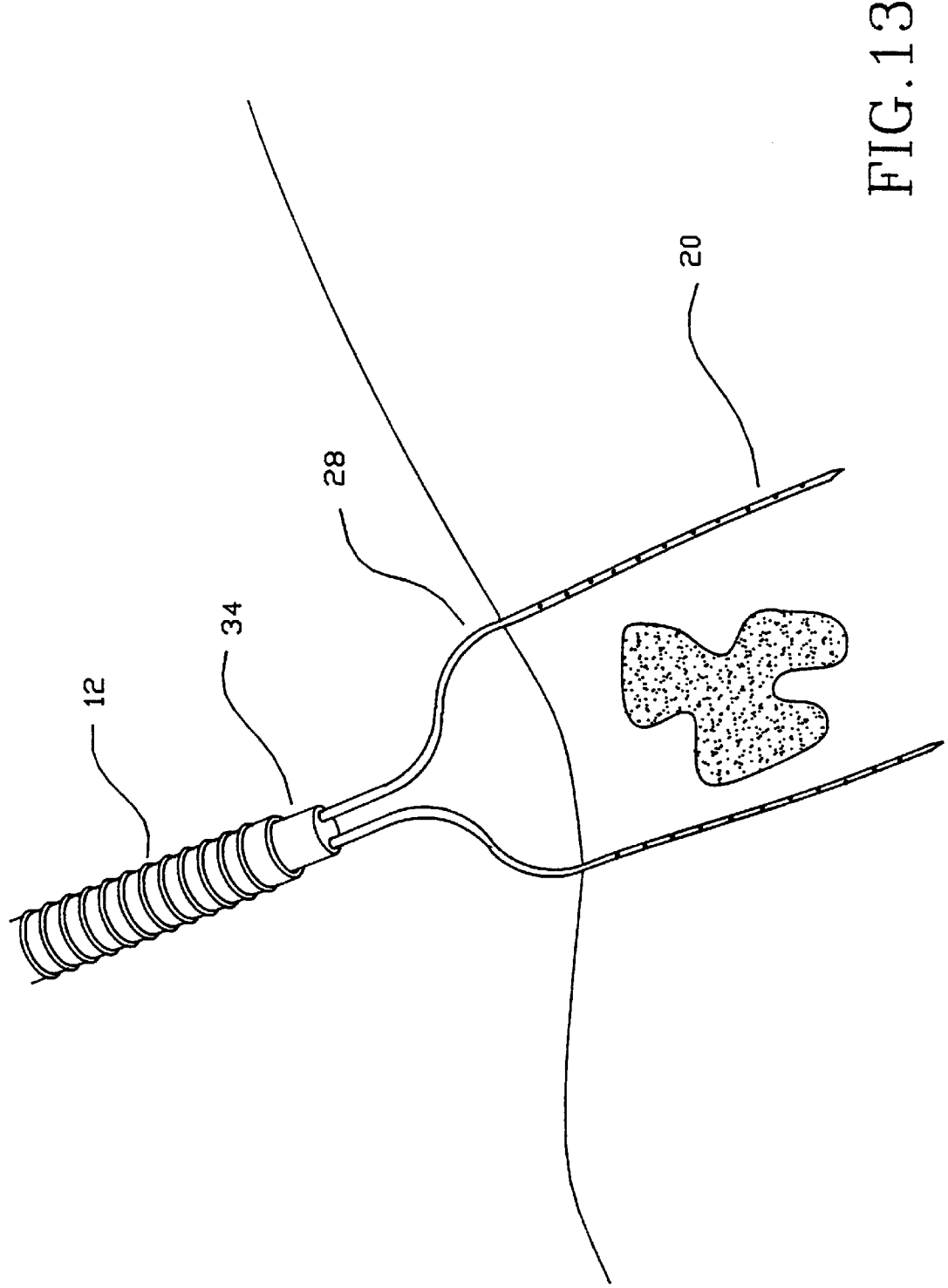
FIG. 13 is a perspective view of the ablation apparatus of the invention, with deployed electrodes surrounding a tumor and defining an ablation volume.

Electrodes 20 are then advanced out of distal end 16 of delivery catheter 12, and become deployed to form a desired ablative volume which surrounds the mass. In FIG. 13, delivery catheter 12 is positioned adjacent to the liver. Electrode deployment device is introduced into delivery catheter 12 with electrode template 34. Electrode deployment device now pierces the liver, and cam 22 advances electrodes 20 out of delivery catheter 12 into deployed positions. Each individual electrode 20 pierces the liver and travels through it until it is positioned in a surrounding relationship to the tumor. The ablative volume is selectable, and determined first by imaging the area to be ablated. The ablative volume is defined by the peripheries of all of the deployed electrodes 20 that surround the exterior of the tumor. Once the volume of ablation is determined, then an electrode set is selected which will become deployed to define the ablation volume. A variety of different factors are important in creating an ablation volume. Primarily, different electrodes 20 will have various degrees of deployment, based on type of electrode material, the level of pre-springing of the electrodes and the geometric configuration of the electrodes in their deployed states. Tissue ablation apparatus 10 permits different electrode 20 sets to be inserted into delivery catheter 12, in order to define a variety of ablation volumes.

Figure 14:
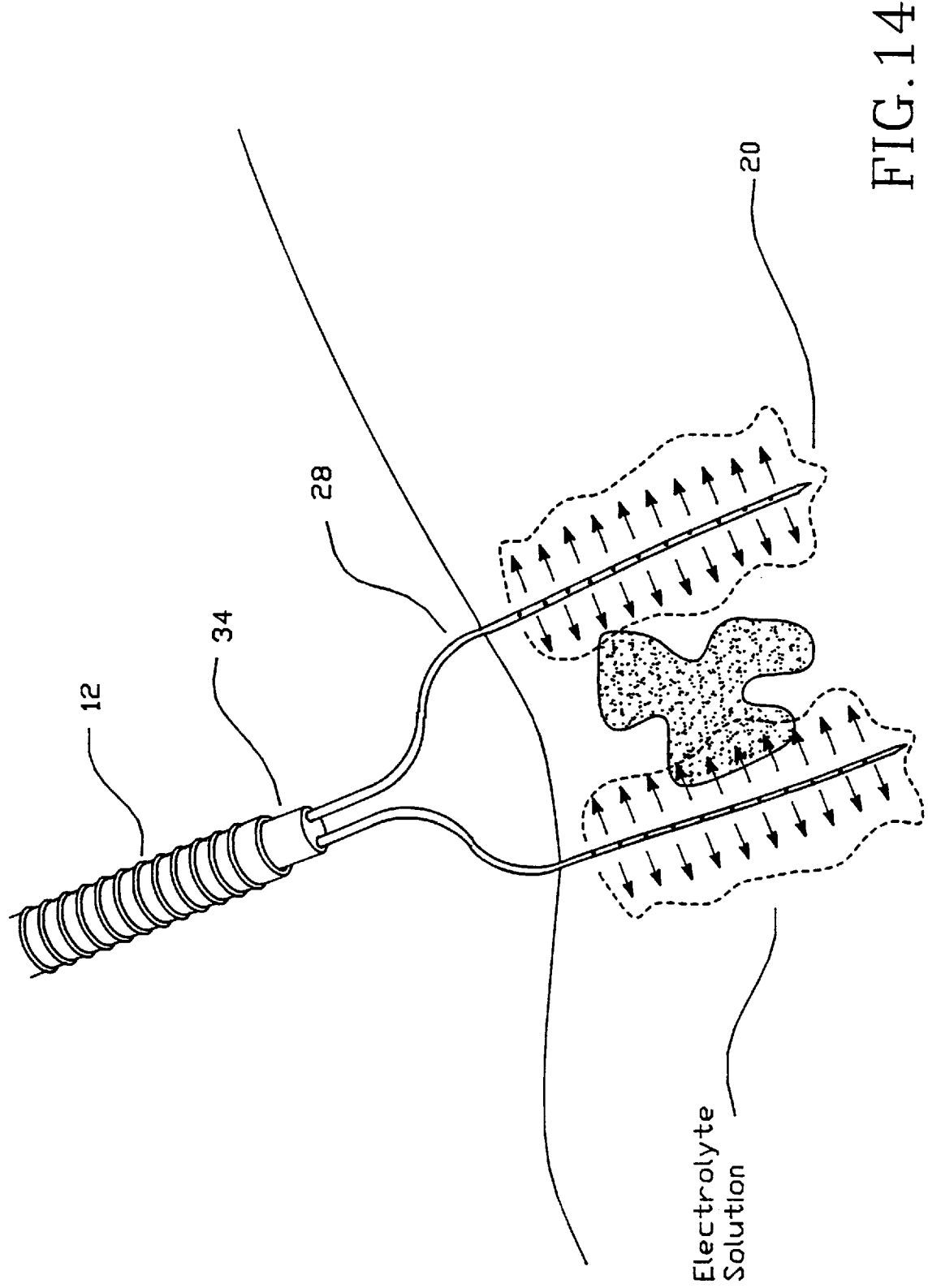
FIG. 14 is a perspective view of the tissue ablation apparatus of the invention shown in FIG. 10, positioned in the body adjacent to the liver, with deployed electrodes surrounding a tumor and infusing a solution to the tumor site during a pre-ablation procedure.
Figure 15:
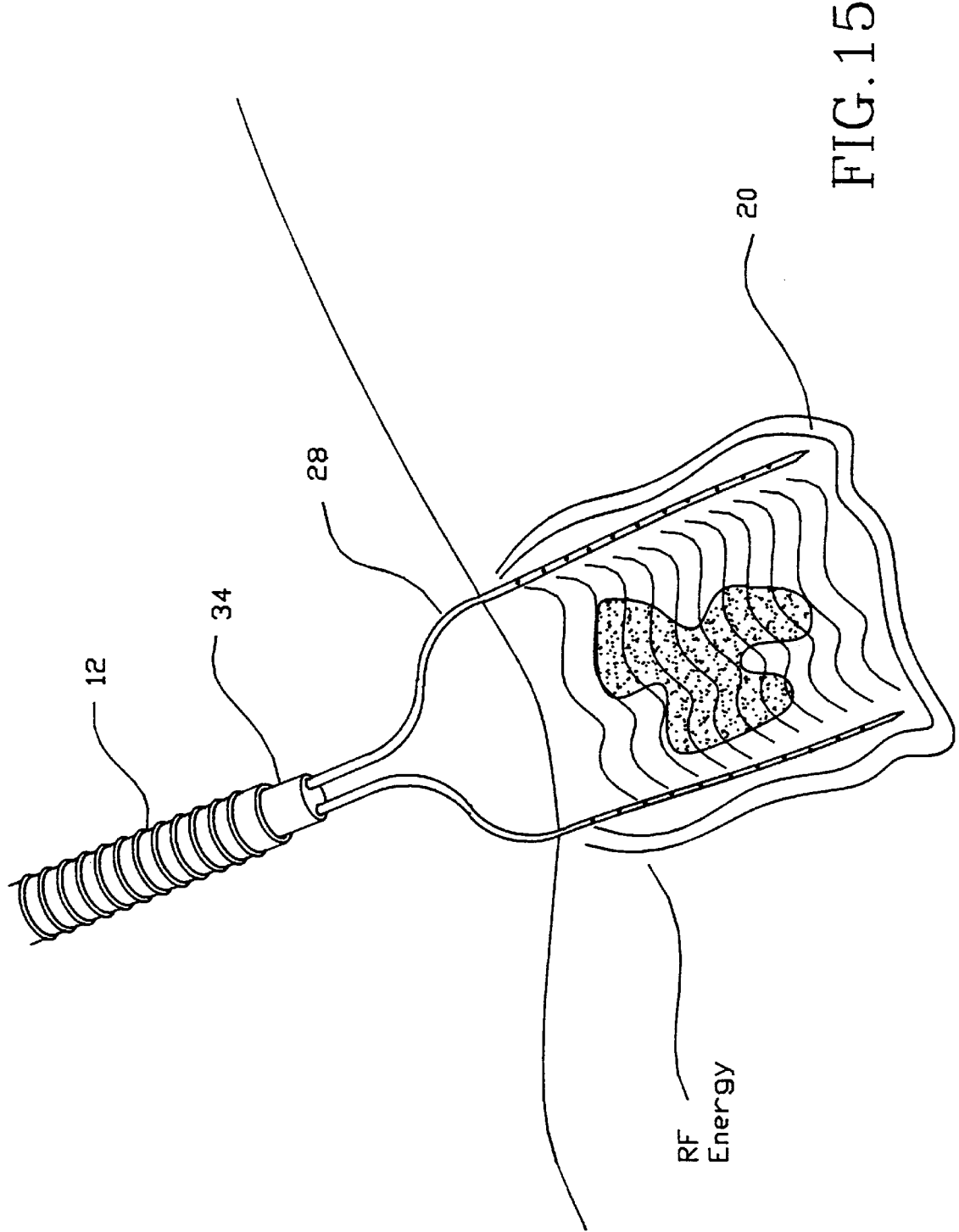
FIG. 15 is a perspective view of the tissue ablation apparatus of the invention shown in FIG. 10, illustrating application of RF energy to the tumor.
Figure 16:
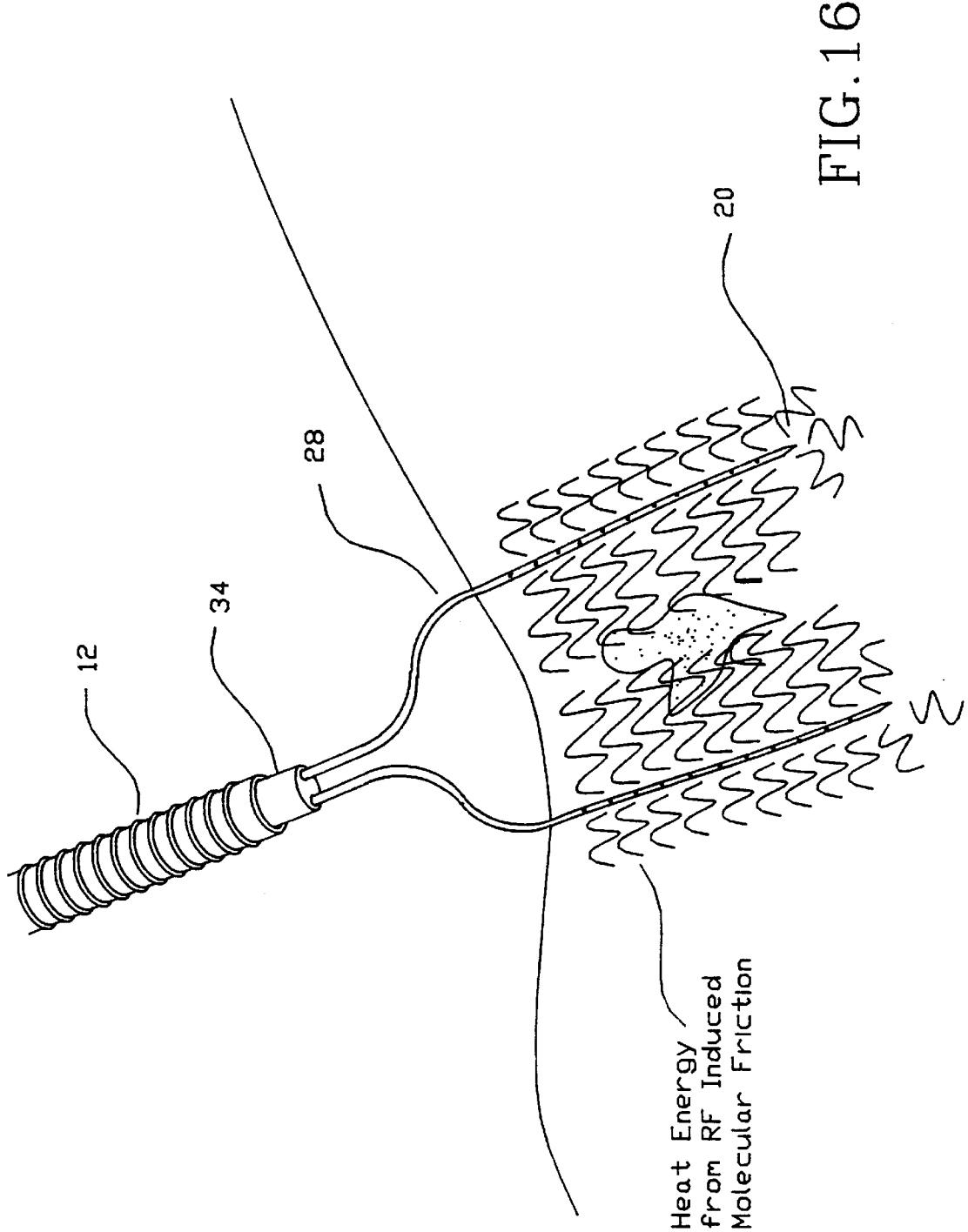
FIG. 16 is a perspective view of the tissue ablation apparatus of the invention, illustrating the electro-desiccation of the tumor.

Prior to ablation of the tumor, a pre-ablation step can be performed. A variety of different solutions, including electrolytic solutions such as saline, can be introduced to the tumor site, as shown in FIG. 14. FIG. 15 illustrates the application of RF energy to the tumor. Electrode insulator 28 is positioned on portions of electrodes 20 where there will be no ablation. This further defines the ablation volume. The actual electro-desiccation of the tumor, or other targeted masses or tissues, is shown in FIG. 16. Again, deployed electrodes 20, with their electrode insulators 28 positioned along sections of the electrodes, define the ablation volume, and the resulting amount of mass that is desiccated.

Figure 17:
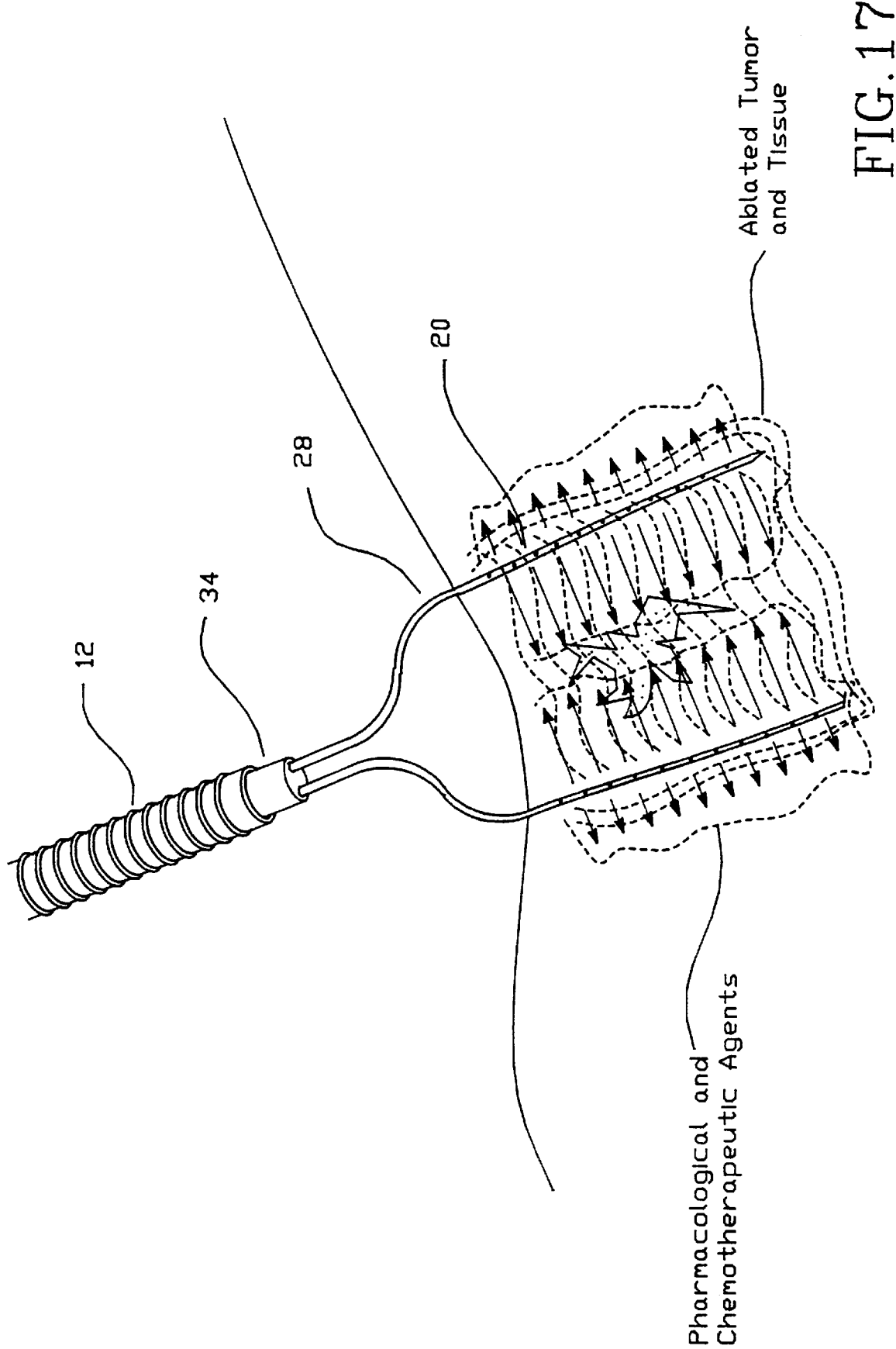
FIG. 17 is a perspective view of the tissue ablation apparatus of the invention, illustrating the instillation of solutions to the tumor site during a postablation procedure.
Figure 18:
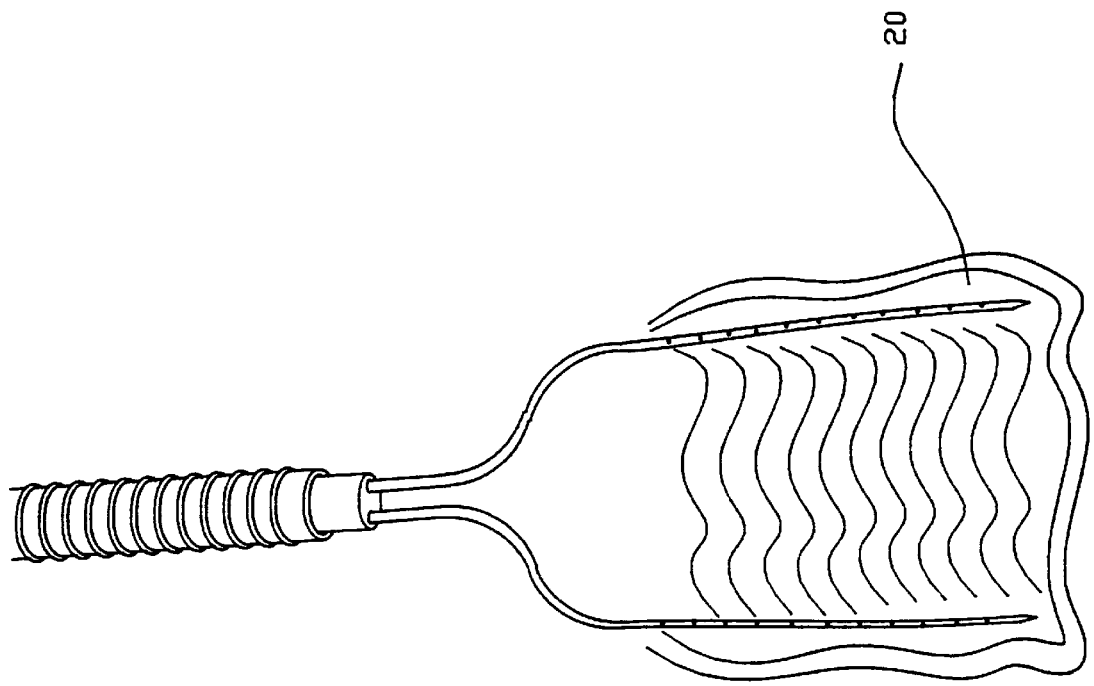
FIG. 18 illustrates bipolar ablation between electrodes of the invention.

Optionally following desiccation, electrodes 20 can introduce a variety of solutions in a post-ablation process. This step is illustrated in FIG. 17. Suitable solutions include but are not limited to chemotherapeutic agents.

Figure 19:
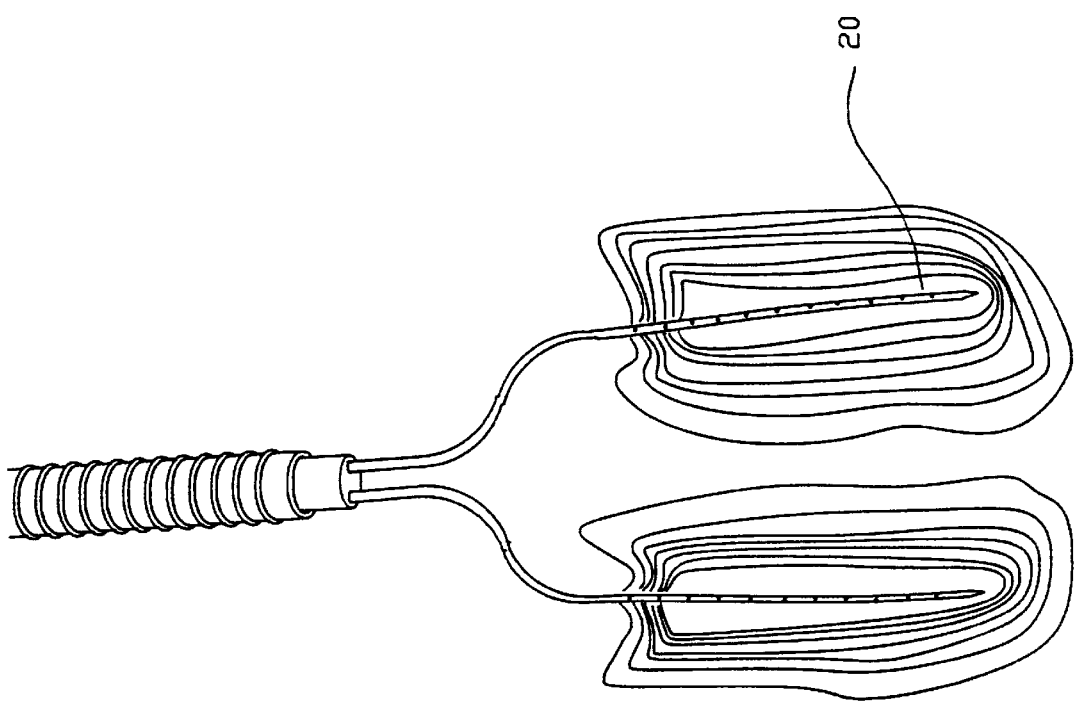
FIG. 19 illustrates monopolar ablation between electrodes of the invention.

FIG. 8 illustrates tissue ablation apparatus 10 operated in a bipolar mode. Its monopolar operation is shown in FIG. 19. Each of the plurality of electrodes 20 can play different roles in the ablation process. There can be polarity shifting between the different electrodes.

Figure 20:
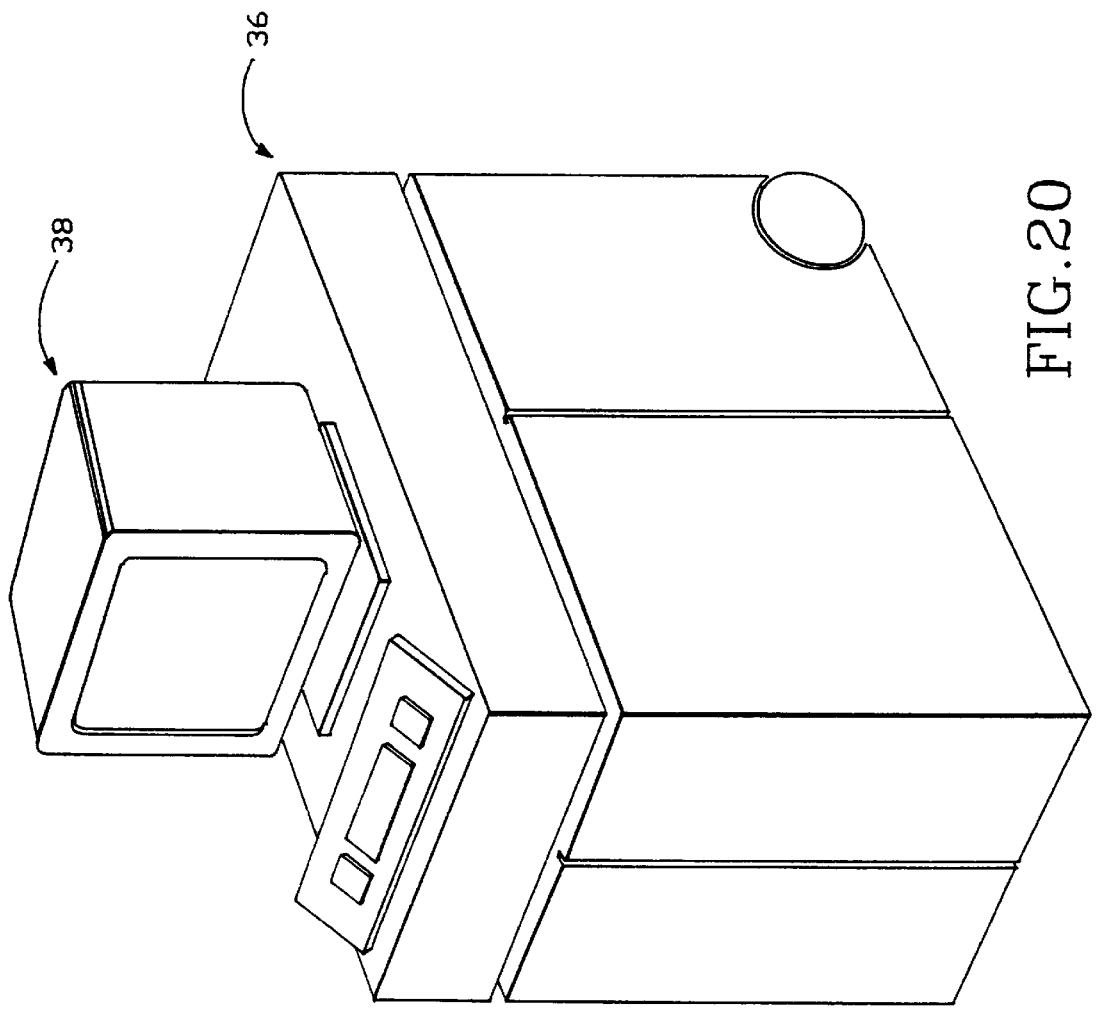
FIG. 20 is a perspective view of an ablation system of the invention, including RF and ultrasound modules, and a monitor.
Figure 21:
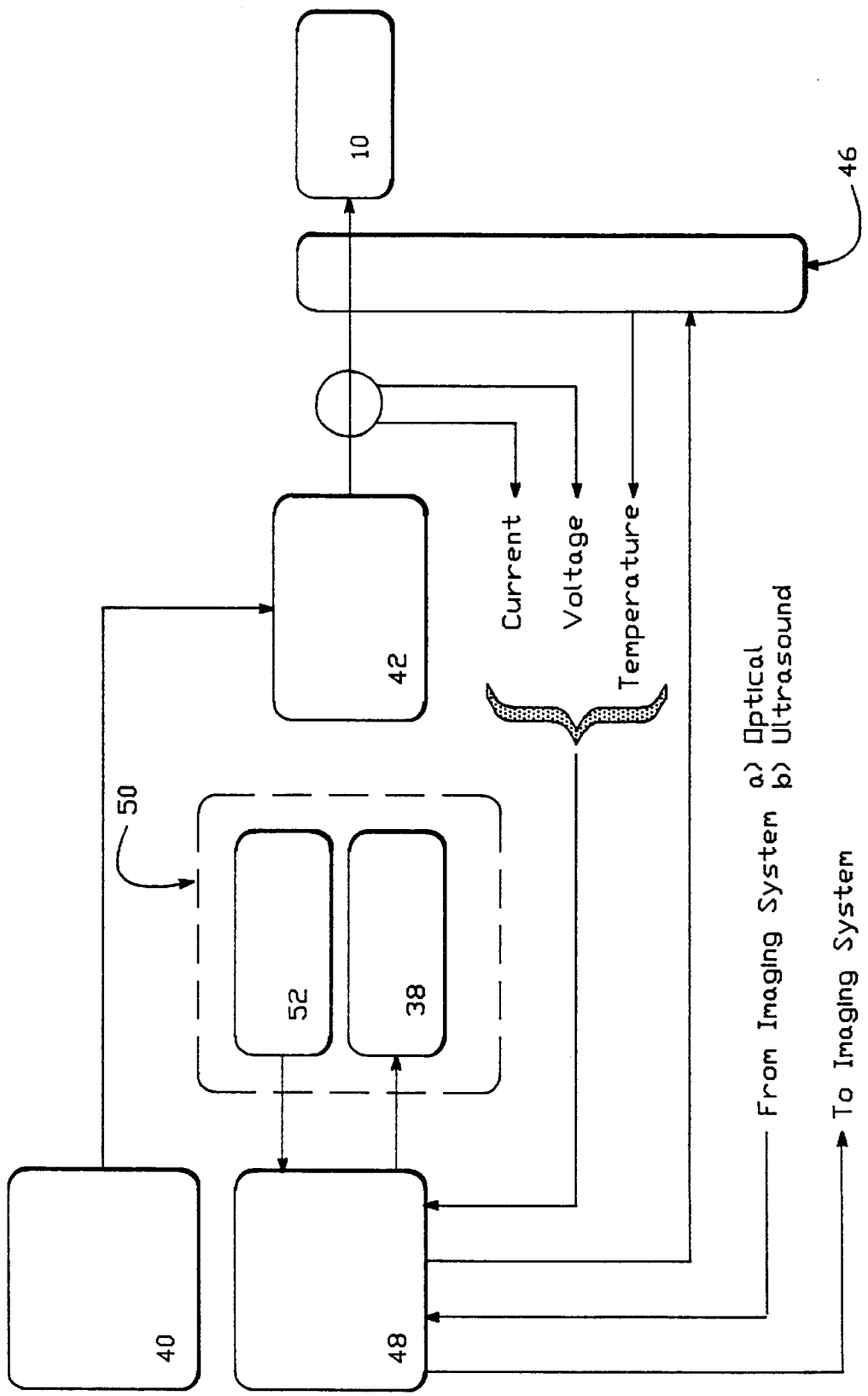
FIG. 21 is a block diagram of the ablation system of the invention.

A tissue ablation system 36, which can be modular, is shown in FIG. 20 and can include a display 38. Tissue ablation system 36 can also include an REF energy source, microwave source, ultrasound source, visualization devices such as cameras and VCR's, electrolytic and chemotherapeutic solution sources, and a controller which can be used to monitor temperature or impedance. One of the deployed electrodes 20 can be a microwave antenna coupled to a microwave source. This electrode can initially be coupled to RF power source 42 and is then switched to the microwave source Referring now to FIG. 21, a power supply 40 delivers energy into RF power generator (source) 42 and then to electrodes 20 of tissue ablation apparatus 10. A multiplexer 46 measures current, voltage and temperature (at numerous temperature sensors which can be positioned on electrodes 20). Multiplexer 46 is driven by a controller 48, which can be a digital or analog controller, or a computer with software. When controller 48 is a computer, it can include a CPU coupled through a system bus. This system can include a keyboard, disk drive, or other non-volatile memory systems, a display, and other peripherals, as known in the art. Also coupled to the bus are a program memory and a data memory.

An operator interface 50 includes operator controls 52 and display 38. Controller 48 is coupled to imaging systems, including ultrasound transducers, temperature sensors, and viewing optics and optical fibers, if included.

Current and voltage are used to calculate impedance. Diagnostics are done through ultrasound, CT scanning, or other methods known in the art. Imaging can be performed before, during and after treatment.

Temperature sensors measure voltage and current that is delivered. The output of these sensors is used by controller 48 to control the delivery of RF power. Controller 48 can also control temperature and power. The amount of RF energy delivered controls the amount of power. A profile of power delivered can be incorporated in controller 38, as well as a pre-set amount of energy to be delivered can also be profiled.

Feedback can be the measurement of impedance or temperature, and occurs either at controller 48 or at electromagnetic energy source 42, e.g., RF or microwave, if it incorporates a controller. For impedance measurement, this can be achieved by supplying a small amount of non-ablation RF energy. Voltage and current are then measured.

Circuitry, software and feedback to controller 48 result in process control and are used to change, (i) power, including RF, ultrasound, and the like, (ii) the duty cycle (on-off and wattage), (iii) monopolar or bipolar energy delivery, (iv) chemotherapeutic and electrolytic solution delivery, flow rate and pressure and (v) determine when ablation is completed through time, temperature and/or impedance. These process variables can be controlled and varied based on temperature monitored at multiple sites, and impedance to current flow that is monitored, indicating changes in current carrying capability of the tissue during the ablative process.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A tissue ablation apparatus, comprising:
   an introducer having a distal portion and a proximal portion;
   an electrode device positionable within an interior of the introducer as the introducer is advanced through tissue, the electrode device including at least a first RF electrode, a second RF electrode and a third RF electrode, each of the first, second and third RF electrodes having a tissue piercing distal end, a non-deployed state when positioned within the introducer and a deployed state when advanced from the distal portion of the introducer, the first, second and third RF electrodes being deployable with curvature from the introducer distal portion and including a section that is perpendicular to a longitudinal axis of the introducer, the first, second and third RF electrodes exhibiting a changing direction of travel along a length of each electrode deployed from the introducer;
   an electrode advancement and retraction member coupled to the electrode device to advance the first, second and third RF electrodes in and out of the introducer distal portion.

2. The apparatus of claim 1, wherein the RF electrodes are retractable in and out of the distal portion of the introducer.

3. The apparatus of claim 1, wherein the ablation volume is defined substantially by the peripheries of the RF electrodes in the deployed state.

4. The apparatus of claim 1, wherein the ablation volume is defined between the RF electrodes in their deployed states.

5. The apparatus of claim 1, wherein the RF electrodes in their deployed state define a three-dimensional ablation volume.

6. The apparatus of claim 1, wherein the RF electrodes are pre-sprung while retained in the introducer such that on being advanced from the distal portion of the introducer the RF electrodes become deployed and fan out from the distal portion of the introducer.

7. The apparatus of claim 1, wherein the RF electrodes are pre-sprung while retained in the introducer such that on being advanced from the distal portion of the introducer the RF electrodes become deployed and fan out from the distal portion of the introducer through tissue in accordance with the curvature.

8. The apparatus of claim 1, wherein each of the RF electrodes changes direction along a length of the electrode in the deployed state.

9. The apparatus of claim 1, wherein at least one of the RF electrodes exhibits, in the deployed state, at least one curved section located near the distal portion of the introducer and a non-curved section beyond the curved section.

10. The apparatus of claim 1, wherein at least one of the RF electrodes exhibits, in the deployed state, a first section which has a first radius of curvature and a second section which extends beyond the first section and has a second radius of curvature.

11. The apparatus of claim 1, wherein at least one of the RF electrodes exhibits, in the deployed state, at least two radii of curvature.

12. The apparatus of claim 1, wherein at least one of the RF electrodes exhibits, in the deployed state, at least two radii of curvature in one plane.

13. The apparatus of claim 1, wherein at least one of the RF electrodes exhibits, in the deployed state, at least two radii of curvature in at least two planes.

14. The apparatus of claim 1, wherein each RF electrode is made of a memory metal or a sprung steel.

15. The apparatus of claim 1. wherein each RF electrode is hollow and includes a fluid distribution port.

16. The apparatus of claim 15, further comprising a source of infusing medium coupled to each of the RF electrodes.

17. The apparatus of claim 15, further comprising a source of chemotherapeutic agent coupled to each of the RF electrodes.

18. The apparatus of claim 1, further comprising an electrode insulator positioned adjacent to and in surrounding relationship to each of the RF electrodes to define an electrode energy delivery surface.

19. The apparatus of claim 1, wherein the electrode advancement and retraction member is removable from the introducer.

20. The apparatus of claim 1, further comprising:
    a handle member coupled to the introducer.

21. The apparatus of claim 1, wherein each RF electrode is wire-like.

22. The apparatus of claim 1, wherein each RF electrode includes a hollow lumen.

23. The apparatus of claim 1, further comprising:
    an energy source coupled to the RF electrodes.

24. The apparatus of claim 23, wherein the energy source is an RF source coupled to the RF electrodes.

25. The apparatus of claim 23 further comprising:
    a thermal sensor coupled to electrode device.

26. The apparatus of claim 1, wherein the first second and third RF electrodes are bipolar RF electrodes.

27. The apparatus of claim 1, wherein the first second and third RF electrodes are monopolar electrodes.

28. A method of deploying electrodes for defining an ablation volume, the method comprising:

providing an ablation apparatus including at least a first RF electrode, a second RF electrode and an introducer with a proximal portion and a distal portion, each of the RF electrodes having a tissue piercing distal end and configured to be advanceable from the introducer distal with curvature from a non-deployed state when positioned within the introducer to a deployed state when advanced from the introducer distal portion, each of the RF electrodes including a section that is perpendicular to a longitudinal axis of the introducer in the deployed state, the first and second RF electrodes exhibiting a changing direction of travel along a length of electrode deployed from the introducer;

positioning the introducer in a solid tissue mass to a selected tissue site; and advancing the first and second RF electrodes from the distal portion of the introducer to the deployed state.

29. The method of claim 28 further comprising:

retracting the RF electrodes in and out of the distal portion of the introducer.

30. The method of claim 28 further comprising:

inserting the RF electrodes into tissue so as to penetrate the tissue.

31. The method of claim 28, wherein the ablation volume is substantially defined by the peripheries of the RF electrodes in the deployed state.

32. The method of claim 28, wherein the ablation volume is defined between the deployed RF electrodes.

33. A method of claim 28 further comprising:

deploying the RF electrodes to define a three-dimensional ablation volume.

34. The method of claim 28 further comprising:

advancing the RF electrodes from the distal portion of the introducer such that the RF electrodes become deployed and fan out from the distal portion.

35. The method of claim 28, wherein the RF electrodes are pre-sprung while retained in the introducer such that on being advanced from the distal portion of the introducer the RF electrodes become deployed and fan out from the distal portion of the introducer through tissue in accordance with the radius of curvature.

36. A method of claim 28, wherein at least one of the RF electrodes changes direction along its length in the deployed state.

37. A tissue ablation apparatus, comprising:

an introducer having a distal portion, a distal end at a distal most position of the distal portion, an introducer aperture formed at the distal end and a proximal portion;

an electrode device positionable within an interior of the introducer as the introducer is advanced through tissue, the electrode device including at least a first RF electrode, a second RF electrode and a third RF electrode, each of the first, second and third RF electrodes having a tissue piercing distal end, a non-deployed state when positioned within the introducer and a deployed state when advanced from the distal end of the introducer, the first, second and third RF electrodes being deployable with cuvature from the introducer distal end and including a section that is perpendicular to a longitudinal axis of the introducer, the first, second and third RF electrodes exhibiting a changing direction of travel along a length of each electrode deployed from the introducer; and an electrode advancement and retraction member coupled to the electrode device, the electrode advancement and retraction member advancing and retracting the RF electrodes in and out of the introducer distal end.

38. A tissue ablation apparatus, comprising:

an introducer having a distal portion, a distal end and a proximal portion;

an electrode device positionable within an interior of the introducer as the introducer is advanced through tissue, the electrode device including at least a first RF electrode, a second RF electrode and a third RF electrode, each of the first, second and third RF electrodes having a non-deployed state when positioned within the introducer and a deployed state when advanced from the distal end of the introducer, the first, second and third RF electrodes being deployable with curvature from the introducer distal end to define an ablation volume, the first, second and third RF electrodes exhibiting a changing direction of travel along a length of each electrode deployed from the introducer; and an electrode advancement and retraction member coupled to the electrode device, the electrode advancement and retraction member advancing and retracting the RF electrodes in and out of the introducer distal end.

39. The apparatus of claim 38, further including an impedance measurement apparatus coupled to the electrode device.

40. A tissue ablation apparatus, comprising:

a rigid introducer having a distal portion and a proximal portion;

an electrode device positionable within an interior of the introducer as the introducer is advanced through tissue, the electrode device including at least a first RF electrode with a tissue piercing distal end and a second RF electrode with a tissue piercing distal end, each of the first and second RF electrodes having a non-deployed state when positioned within the introducer and a deployed state when advanced from the distal portion of the introducer, the first and second RF electrodes being deployable with curvature from the introducer distal portion, the first and second RF electrodes exhibiting a changing direction of travel along a length of each electrode deployed from the introducer; and an electrode advancement and retraction member coupled to the electrode device, the electrode advancement and retraction member advancing and retracting the RF electrodes in and out of the introducer distal portion.

41. A tissue ablation apparatus, comprising:

an introducer having a distal portion and a proximal portion;

an electrode device positionable within an interior of the introducer as the introducer is advanced through tissue, the electrode device including at least a first RF electrode with a tissue piercing distal end, a second RF electrode with a tissue piercing distal end and an electrode coupling, each of the first and second RF electrodes having a non-deployed state when positioned within the introducer and a deployed state when advanced from the distal portion of the introducer, the first and second RF electrodes being deployable with curvature from the introducer distal portion, the first and second RF electrodes exhibiting a changing direction of travel along a length of each electrode deployed from the introducer; and an electrode advancement and retraction member coupled to the electrode device, the electrode advancement and retraction member advancing and retracting the RF electrodes in and out of the introducer distal end, wherein the electrode device is physically coupled to the electrode advancement and retraction member.

42. The apparatus of claim 41, wherein the electrode advancement member is a rigid electrode introducer.

43. The apparatus of claim 42, further comprising:

a handpiece coupled of the rigid electrode introducer.

44. The apparatus of claim 43, wherein the rigid electrode introducer is coupled to the handpiece.

45. A tissue ablation apparatus, comprising:

an introducer having a distal portion and a proximal portion;

an obturator with a tissue piercing distal end, the obturator being positionable in an interior of the introducer as the obturator is advanced through tissue;

an electrode device positionable within the interior of the introducer, the electrode device including at least a first RF electrode, a second RF electrode and a third RF electrode, each of the first, second and third RF electrodes having a tissue piercing distal end, a non-deployed state when positioned within the introducer and a deployed state when advanced from the distal portion of the introducer, the first, second and third RF electrodes being deployable with curvature from the introducer distal portion and including a section that is perpendicular to a longitudinal axis of the introducer, the first, second and third RF electrodes exhibiting a changing direction of travel along a length of each electrode deployed from the introducer; and an electrode advancement and retraction member coupled to the electrode device to advance the first, second and third RF electrodes in and out of the introducer distal portion.

46. A tissue ablation apparatus, comprising:

an introducer having a distal portion and a proximal portion;

an obturator with a tissue piercing distal end, the obturator being positionable in an interior of the introducer as the obturator is advanced through tissue;

an electrode device positionable within the interior of the introducer, the electrode device including an electrode housing and at least a first RF electrode, a second RF electrode and a third RF electrode positionable in the electrode housing, each of the first, second and third RF electrodes having a tissue piercing distal end, a non-deployed state when positioned within the electrode housing and a deployed state when advanced from the distal portion of the introducer, the first, second and third RF electrodes being deployable with curvature from the introducer distal portion and including a section that is perpendicular to a longitudinal axis of the introducer, the first, second and third RF electrodes exhibiting a changing direction of travel along a length of each electrode deployed from the introducer; and an electrode advancement and retraction member coupled to the electrode device to advance the first, second and third RF electrodes in and out of the introducer distal portion.

* * * * *